(12) United States Patent
Doan

(10) Patent No.: US 7,974,675 B2
(45) Date of Patent: Jul. 5, 2011

(54) METHOD OF MEASURING PRESSURE WITH A SEPTAL LEAD

(75) Inventor: Phong D. Doan, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 213 days.

(21) Appl. No.: 12/395,442

(22) Filed: Feb. 27, 2009

(65) Prior Publication Data

US 2009/0163822 A1 Jun. 25, 2009

Related U.S. Application Data

(62) Division of application No. 11/222,872, filed on Sep. 9, 2005, now Pat. No. 7,515,971.

(51) Int. Cl.
*A61N 1/05* (2006.01)
*A61B 1/04* (2006.01)

(52) U.S. Cl. .................. 600/375; 607/119; 607/126

(58) Field of Classification Search .................. 600/375; 607/116, 119, 122, 126, 128
See application file for complete search history.

(56) References Cited

U.S. PATENT DOCUMENTS

| | | | |
|---|---|---|---|
| 4,269,198 A | 5/1981 | Stokes | |
| 4,578,076 A | 3/1986 | Luukkainen et al. | |
| 4,712,555 A | 12/1987 | Thornander et al. | |
| 4,721,118 A | 1/1988 | Harris | |
| 4,788,980 A | 12/1988 | Mann et al. | |
| 4,841,971 A | 6/1989 | Hess | |
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 5,545,206 A | 8/1996 | Carson | |
| 5,755,767 A | 5/1998 | Doan et al. | |
| 5,853,422 A | 12/1998 | Huebsch et al. | |
| 5,855,592 A | 1/1999 | McGee et al. | |
| 6,240,322 B1 | 5/2001 | Peterfeso et al. | |
| 6,241,726 B1 | 6/2001 | Chia et al. | |
| 6,253,110 B1 | 6/2001 | Brabec et al. | |
| 6,328,699 B1 | 12/2001 | Eigler et al. | |
| 6,584,362 B1 | 6/2003 | Scheiner et al. | |

(Continued)

FOREIGN PATENT DOCUMENTS

WO 0151123 A1 7/2001

(Continued)

OTHER PUBLICATIONS

NonFinal Office Action, mailed Dec. 31, 2007: U.S. Appl. No. 11/222,875.

(Continued)

*Primary Examiner* — Scott M Getzow
*Assistant Examiner* — Joseph M Dietrich

(57) ABSTRACT

A method of measuring pressure through a septum in a patient's heart is provided. A lead inserted into the right side of a heart is routed through the septum to gain access to the left side of the heart. The lead includes a mounting mechanism that secures the lead to one or both sides of the septal walls. The lead also includes one or more sensors for measuring cardiac pressure on the left side of the heart and, as necessary, the right side of the heart.

9 Claims, 20 Drawing Sheets

U.S. PATENT DOCUMENTS

| | | |
|---|---|---|
| 6,611,710 B2 | 8/2003 | Gomperz et al. |
| 6,643,546 B2 | 11/2003 | Mathis et al. |
| 6,669,693 B2 | 12/2003 | Friedman |
| 7,515,971 B1 | 4/2009 | Doan |
| 2002/0077555 A1 | 6/2002 | Schwartz |
| 2003/0055344 A1 | 3/2003 | Eigler et al. |
| 2003/0055345 A1 | 3/2003 | Eigler et al. |
| 2003/0195600 A1 | 10/2003 | Tronnes et al. |
| 2004/0116992 A1* | 6/2004 | Wardle et al. ............ 607/116 |
| 2004/0147969 A1 | 7/2004 | Mann et al. |
| 2004/0167580 A1 | 8/2004 | Mann et al. |
| 2004/0249429 A1 | 12/2004 | Tadlock |
| 2004/0260371 A1 | 12/2004 | Greenland et al. |
| 2005/0060014 A1 | 3/2005 | Swoyer et al. |
| 2005/0085883 A1 | 4/2005 | Ollivier et al. |
| 2005/0096718 A1 | 5/2005 | Gerber et al. |

FOREIGN PATENT DOCUMENTS

| | | |
|---|---|---|
| WO | 2005000206 A2 | 1/2005 |
| WO | 2005000206 A3 | 1/2005 |

OTHER PUBLICATIONS

NonFinal Office Action, mailed Jul. 9, 2008: U.S. Appl. No. 11/222,875.

Notice of Allowance, mailed Dec. 5, 2008: U.S. Appl. No. 11/222,875.

NonFinal Office Action, mailed Jul. 11, 2007: U.S. Appl. No. 11/223,382.

NonFinal Office Action, mailed Dec. 26, 2007: U.S. Appl. No. 11/223,382.

* cited by examiner

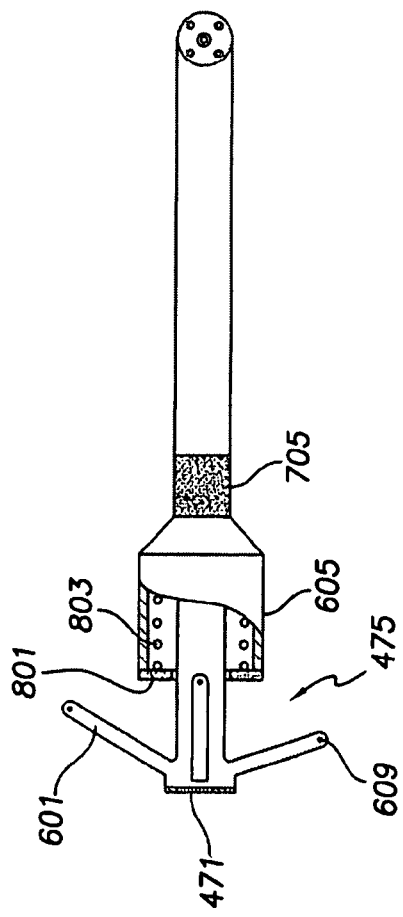
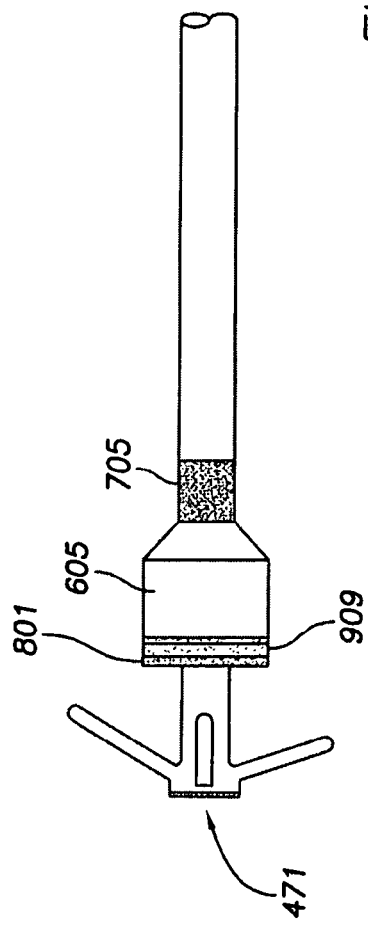

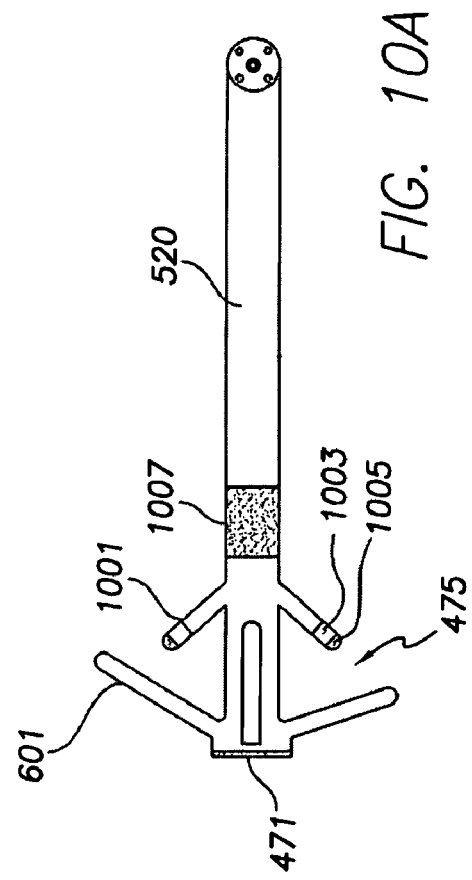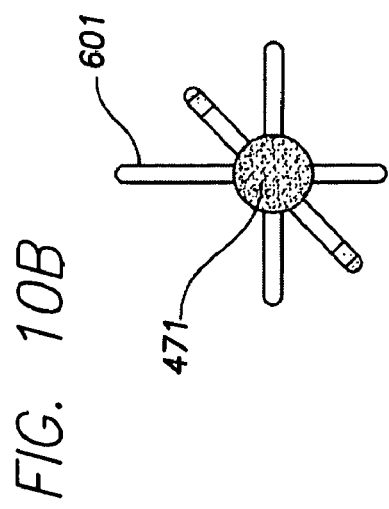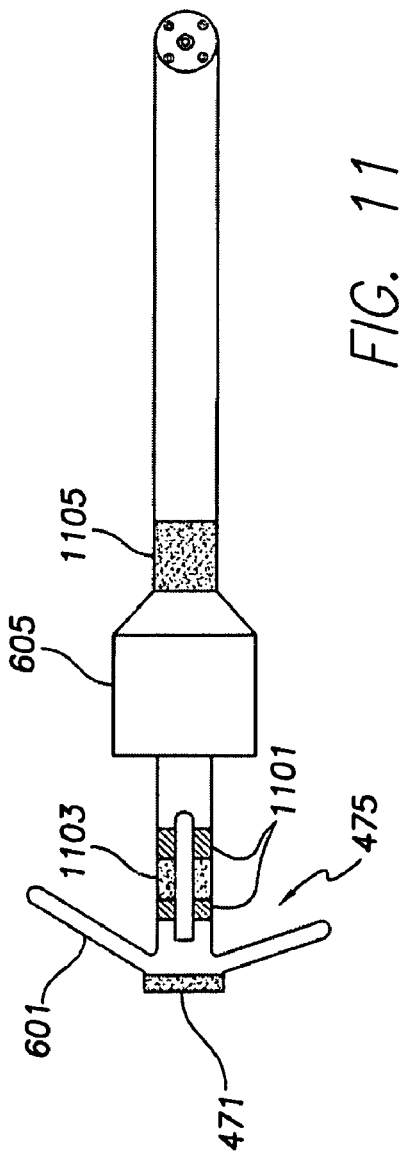

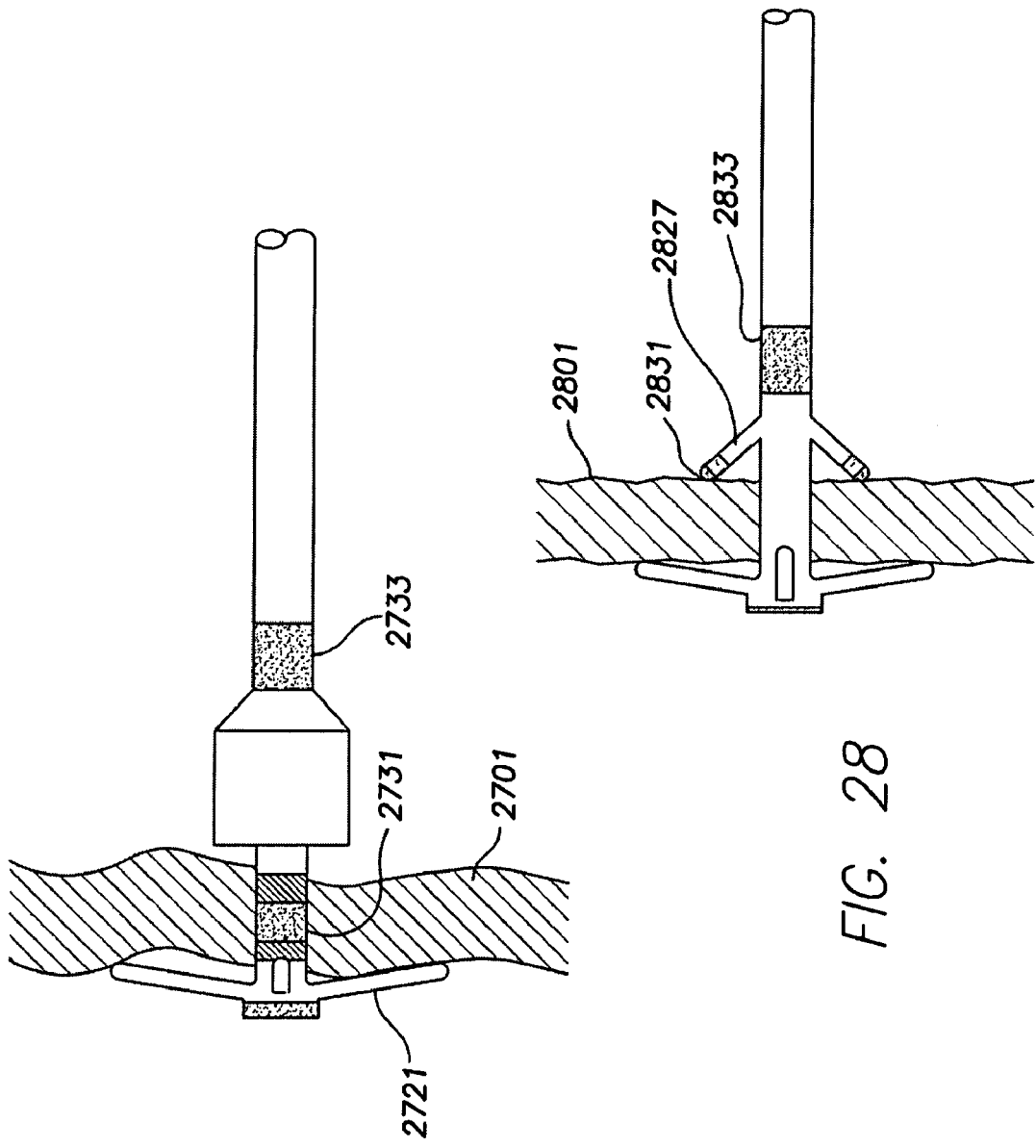

METHOD OF MEASURING PRESSURE WITH A SEPTAL LEAD

CROSS REFERENCE TO RELATED APPLICATIONS

This application is a divisional of U.S. patent application Ser. No. 11/222,872, filed Sep. 9, 2005, titled "Left Atrial Pressure Sensor Lead"; and is related to U.S. patent application Ser. No. 11/223,382, filed Sep. 9, 2005, titled "Left Atrial Pressure Sensor Lead, now abandoned.

TECHNICAL FIELD

This application relates generally to implantable cardiac stimulation devices and, more specifically, to a lead system implanted through a septal wall.

BACKGROUND

When a person's heart does not function normally due to, for example, a genetic or acquired condition various treatments may be prescribed to correct or compensate for the condition. For example, pharmaceutical therapy may be prescribed for a patient or a pacemaker may be implanted in the patient to improve the operation of the patient's heart.

In conjunction with such therapy it may be desirable to measure pressure in one or more chambers of the heart. For example, absolute cardiac pressure may be used as an indicator for several potentially lethal cardiac conditions. By measuring cardiac pressure, abnormal conditions such as these may be detected and in some cases the patient's therapy may be modified to compensate for the abnormal conditions. As an example, if cardiac pressure is continuously measured, the operation of an implanted device such as a pacemaker may be adjusted, as necessary, according to conditions diagnosed as a result of the pressure measurements.

Conventionally, pressure sensing devices have been used to measure pressures on the right side of the heart. However, measurements of right side pressure may not provide sufficient indications for detection of conditions such as congestive heart failure, hypertension and mitral valve defects. In particular, left atrial pressure has been identified as an excellent indicator for left ventricular failure.

Obtaining pressure measurements from the left side of the heart presents several challenges. First, access to the left side of the heart must be provided in a safe manner. In addition, the pressure sensors need to be implanted in a manner that ensures accurate pressure measurements may be made. Again, the use of a safe implantation technique is a primary consideration. Accordingly, a need exists for improved structures and techniques for measuring cardiac pressure.

SUMMARY

The invention relates to an apparatus for and method of measuring pressure in a chamber on the left side of a patient's heart. Access to the left chamber may be gained through a wall in the heart.

In some embodiments, a lead includes a sensor and a mounting mechanism on a distal end. The distal end of the lead may be routed from a right side of the heart through a hole in a wall to the left side of the heart. At least a portion of the mounting mechanism and the sensor may thereby be positioned in the left side of the heart.

In some embodiments, a mounting mechanism includes a first set of tines. The first set of tines may, for example, extend from a distal portion of a lead. In some embodiments, the first set of tines is positioned against a wall on the left side of the heart.

In some embodiments, a mounting mechanism comprises a proximal base. The tines press the septal wall against the proximal base to secure a head portion of the lead.

In some embodiments, the lead includes a biasing mechanism in the proximal base. The biasing mechanism may be adapted to press the mounting mechanism against the left side of the wall.

In some embodiments, the mounting mechanism includes a second set of tines acting on the other side of the septal wall from the first set of tines to hold the lead in place by clamping the septal wall between the two pairs of tines.

In some embodiments, the mounting mechanism includes a set of arms having two sets of spaced apart protrusions. The arms fold from a position pointing away from the distal tip of the lead to an extended position pointing in the same direction as the distal tip of the lead. The arms may be pulled partially through the septal wall when extended to secure the septal wall between the two sets of protrusions.

In some embodiments, a set of electrodes may be placed on the structures of the mounting mechanism and/or lead near the distal end of the lead. Complementary cathodes and anode electrodes may be present.

In some embodiments, medicated sleeves or materials impregnated with medication may be placed in or on the structures of the distal end of the lead and/or the mounting mechanism.

These and other features, aspects and advantages of the invention will be more fully understood when considered with respect to the following detailed description, appended claims and accompanying drawings.

BRIEF DESCRIPTION OF THE DRAWINGS

Embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

FIG. 8 is a diagram of one embodiment of a head portion of a lead having a spring.

FIG. 9 is a diagram of one embodiment of a head portion of a lead having a medicating sleeve.

FIG. 10A is a diagram of one embodiment of a head portion of a lead having a second set of tines.

FIG. 10B is an end view of one embodiment of a head portion of a lead having a second set of tines.

FIG. 11 is a diagram of one embodiment of a head portion of a lead.

FIG. 27 is an illustration of a lead secured in the septal wall.

FIG. 28 is an illustration of a lead secured in the septal wall.

Figure 1:
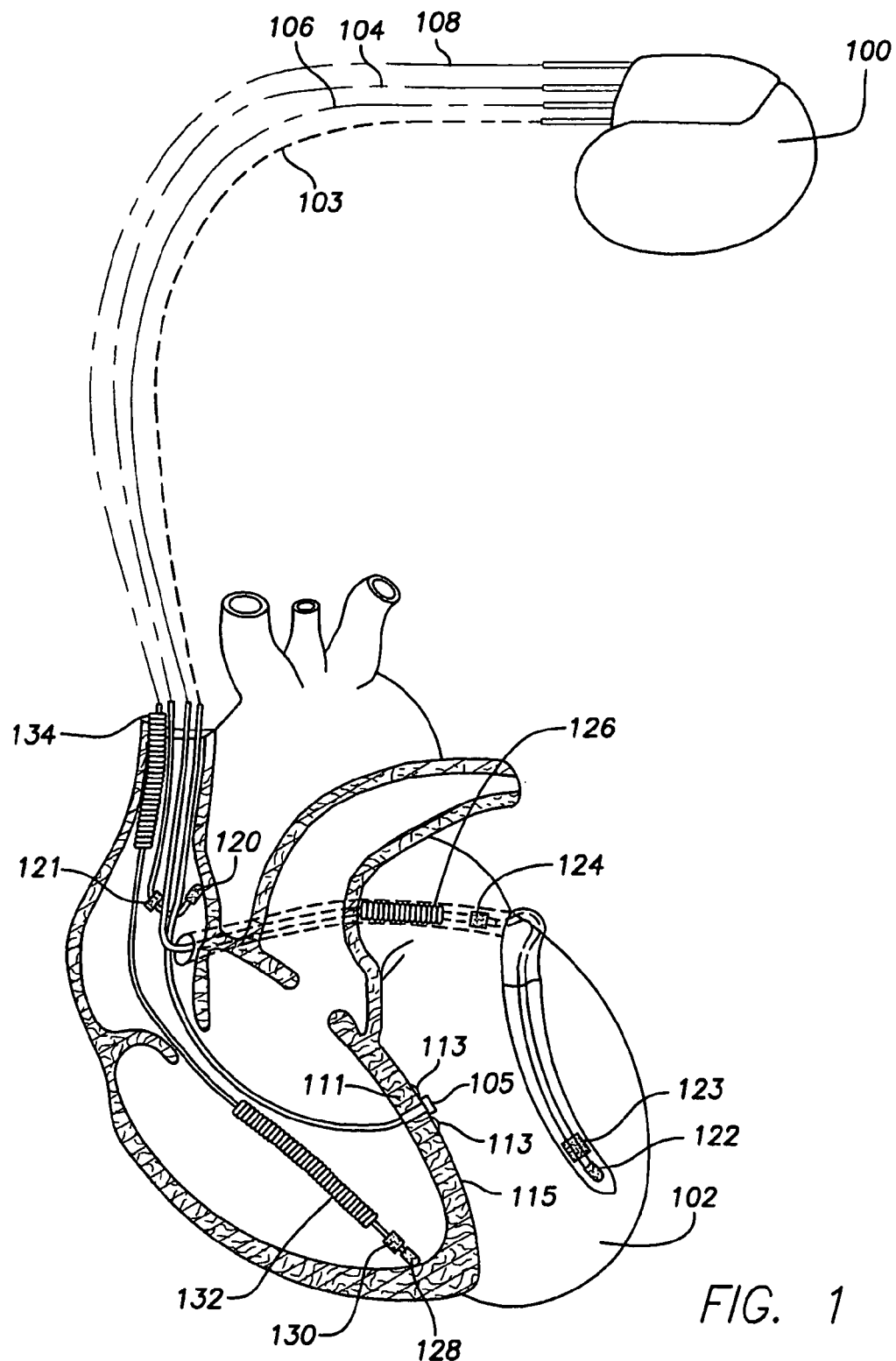
FIG. 1 is a simplified diagram of one embodiment of an implantable stimulation device in electrical communication with several leads implanted in a patient's heart for measuring pressure and delivering multi-chamber stimulation and shock therapy.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Also, like reference numerals denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

Referring to FIG. 1, in one aspect the invention relates to an implantable cardiac device that includes one or more leads (e.g., lead 103) that are implanted in a patient. The lead 103 consists of a lead body and at least one lead head and includes at least one sensor 105 for measuring pressure in the patient's heart. The implantable cardiac device includes circuitry (e.g., in a stimulation device 100) that processes signals from the sensor 105 to determine relative cardiac pressure.

Figure 3:
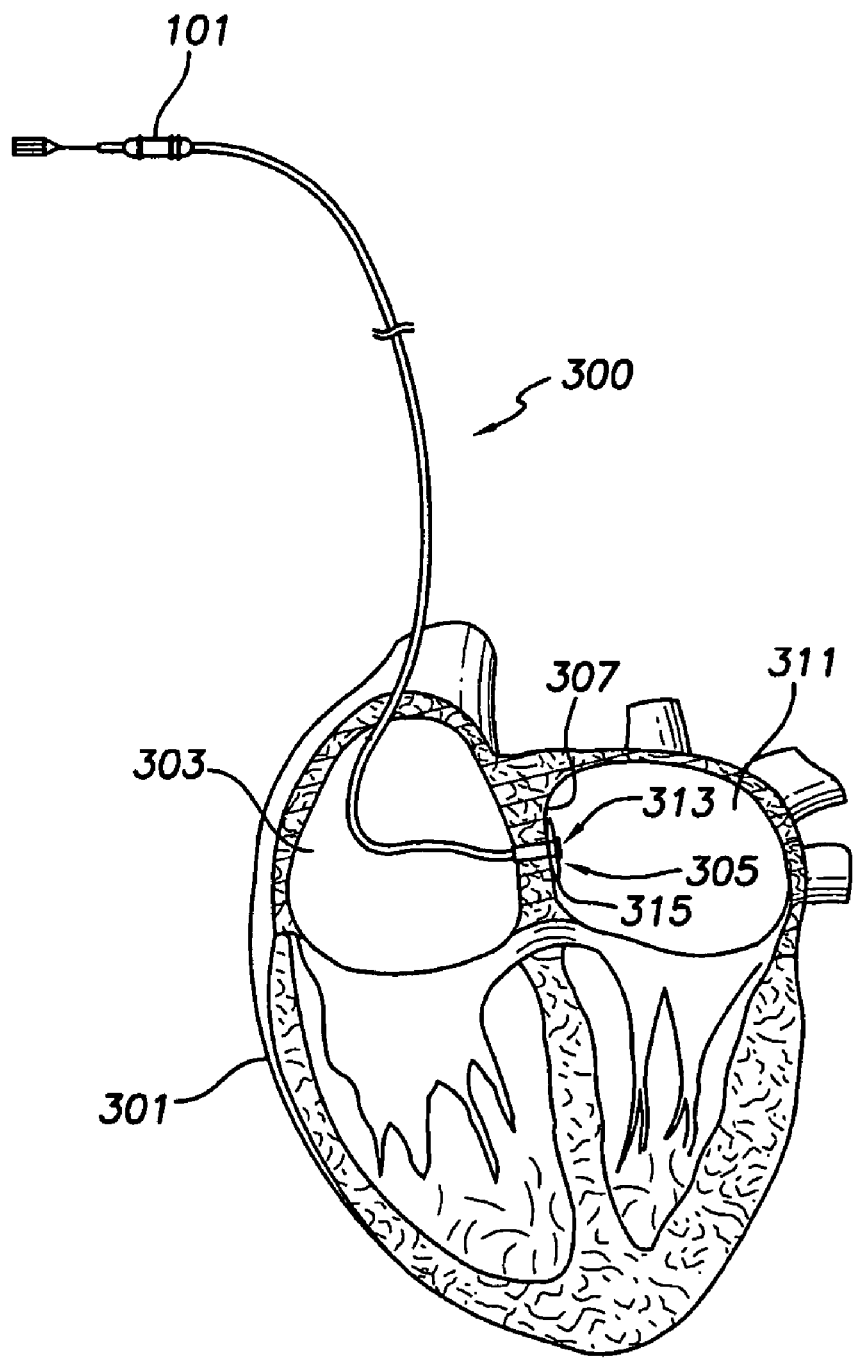
FIG. 3 is a simplified diagram of one embodiment of a cardiac lead having a mounting mechanism that is implanted through a septum.

In embodiments where the lead is initially routed into the right side of the heart, pressure may be measured in the left side of the heart (e.g., the left atrium, left ventricle or aorta) by routing the lead through a wall in the heart (e.g., the ventricular septum 111 or the atrial septum 307 shown in FIG. 3). For example, a hole may be created in the septum by piercing the septum using a piercing device such as a needle.

After a distal portion of the lead 103 is maneuvered through the septum 111, a mounting mechanism 113 that expands from the lead 103 is positioned against a wall 115 on the left side of the septum 111. A mounting mechanism may take many forms including, for example, one or more tines. Additional details of an exemplary stimulation device 100 and associated leads will be discussed in conjunction with FIGS. 1 and 2.

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having, for example, an atrial tip electrode 120, which typically is implanted in the patient's right atrial appendage or septum. FIG. 1 shows the right atrial lead 104 as having an optional atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using, for example, a left ventricular tip electrode 122, left ventricular ring electrode 123, left atrial pacing therapy using, for example, a left atrial ring electrode 124, and shocking therapy using, for example, a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
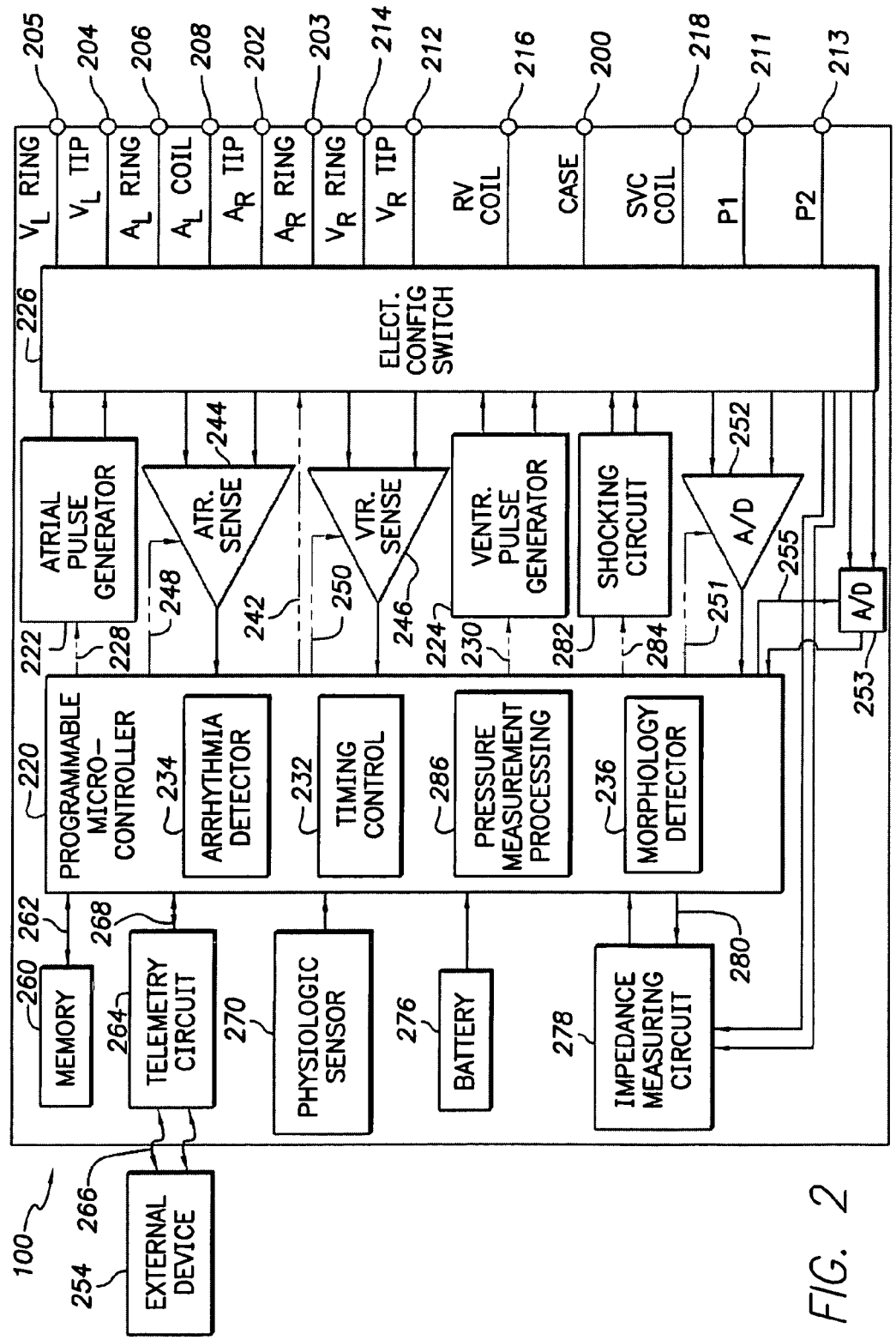
FIG. 2 is a simplified functional block diagram of one embodiment of a multi-chamber implantable stimulation device constructed in accordance with the invention, illustrating basic elements that are configured to provide pressure sensing, cardioversion, defibrillation or pacing stimulation or any combination thereof.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 203, 204, 205, 206, 208, 211, 212, 213, 214, 216, and 218 (shown schematically and, for convenience, the names of the electrodes to which they are connected are shown next to the terminals).

To achieve right atrial sensing and pacing, the connector includes, for example, a right atrial tip terminal (A$_R$ TIP) 202 adapted for connection to the atrial tip electrode 120. A right atrial ring terminal (A$_R$ RING) 203 may also be included adapted for connection to the atrial ring electrode 121. To achieve left chamber sensing, pacing, and shocking, the connector includes, for example, a left ventricular tip terminal (V$_L$ TIP) 204, left ventricular ring terminal (V$_L$ RING) 205, a left atrial ring terminal (A$_L$ RING) 206, and a left atrial shocking terminal (A$_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (V$_R$ TIP) 212, a right ventricular ring terminal (V$_R$ RING) 214, a right ventricular shocking terminal (R$_V$ COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module; the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiologic sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiologic sensors 270 optionally include sensors to help detect movement and minute ventilation in the patient. The physiologic sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium or similar battery technology.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through, for example, two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In some embodiments device 100 also may include circuitry for processing signals from one or more pressure sensors. Depending upon the application, the pressure sensors may be implanted in the heart, in other locations in the patient such as the thoracic cavity, anywhere along a lead or within the housing 200.

A typical pressure sensor generates electrical signals indicative of changes in a sensed pressure. Thus, one or more wires may be used to connect a sensor to the device 100. FIG. 2 illustrates an embodiment where two pressure signals P1 and P2 are coupled to the device 100 via terminals 211 and 213, respectively. An analog-to-digital (A/D) data acquisition system 253 may be configured (e.g., via signal line 255) to acquire and amplify the signals P1 and P2, convert the raw analog data into a digital signal, filter the signals and store the digital signals for later processing by, for example, a pressure measurement processing component 286 and/or telemetric transmission to an external device 254. Referring now to FIGS. 3-28, various embodiments of leads that may be used to measure pressure across a septal wall will be discussed.

FIG. 3 is a diagram of one embodiment of a lead 300 and sensor 313 implanted into a left atrium 311 through the septal wall 307 of the heart 301. In one embodiment, the lead 300 includes a proximal end with a housing 101 that may enclose one or more electrical connectors, openings to lumens or other components and structures. The housing 101 may be formed as a connector to allow the lead 300 to be connected to an external device. The electrical connectors may be coupled to electrical conductors such as wires that run the length of the lead 300. For example, the conductors may connect to the sensor 313. The lead 300 may include one or more lumens that run the length of the lead 300 or over a portion of the length of the lead 300. The lumens may house the electrical conductors, removable guidewires and other components.

In one embodiment, the lead 300 may reach the heart of the patient intravenously. The lead 300 may be partially disposed in a vein of a patient that leads to the right atrium. The distal end of the lead 300 may be partially disposed in the right atrium 303 of the heart 301 with a head portion 305 of the lead 300 partially in the left atrium 311. The head portion 305 of lead 300 may include a sensor 313. The sensor 313 may detect the fluid pressure in the left atrium 311.

In one embodiment, the head portion 305 of the lead 300 may be situated through the septal wall 307 in the region of the fossa ovalis. The fossa ovalis is typically the thinnest section of the atrial septal wall 307. The head portion 305 may be held in place by a mounting mechanism 315. The mounting mechanism 315 and installation of the lead into a patient is discussed in greater detail below. The sensor 313 may be used to accurately measure pressure in the left atrium 311. In another embodiment, the lead 300 also may include additional pressure sensors positioned in the right atrium 303 or in other structures of the heart 301. The lead 300 may house additional sensors in other parts of the lead 300.

In one embodiment, the portion 305 of the lead 300 situated in the left atrium 311 may be designed to have a relatively low profile against the septal wall 307. In this way, problems associated with protruding objects inside of the heart 301 may be avoided. For example, blood clots may form on an object that protrudes from a wall of the heart 301. If these blood clots break loose in the left side of the heart the blood clots may travel to other areas of the body such as the brain and cause a blockage in a blood vessel (i.e., an embolism).

If a structure in the heart 301 has a low profile against a wall of the heart 301, the body may quickly build up a biological layer of endothelial cells ("the intima") over the structure. As a result, the likelihood of blood clots breaking loose may be significantly reduced as compared to structures that protrude relatively deeply into the left side of the heart. The buildup of the intima also may assist in firmly attaching a structure to the septal wall 307. As a result, the structure may be attached to the heart 301 in a sufficiently stable manner so as to prevent injury to the heart 301. The lead head portion 305, sensor 313 and mounting mechanism 315 have a low profile to diminish the problem of blood clots and to take advantage of intima build up to secure the sensor 313 in the left atrium 311.

In one embodiment, the lead 300 provides a secure and safe attachment to the septal wall 307 that may be used in combination with other leads and sensors implanted in the patient, by an external monitoring device to provide a variety of pressure measurements in real time. These cardiac pressure measurements may provide valuable information for diagnosing a variety of cardiac problems. Examples of cardiac problems that may be associated high pressure measurements in the left atrium 311 include mitral stenosis and left ventricle failure. When diagnoses such as these are used in conjunction with a heart stimulation device, appropriate therapy such as cardiac resynchronization therapy may be immediately delivered to the patient.

In another embodiment, the lead 300 may have additional sensors placed throughout the length of the lead 300. For example, a sensor may be placed in the body of the lead 300 such that it would be positioned in the right atrium 303 when the tip is in position in the left atrium 311. This set up may be employed to generate highly accurate pressure measurements because the number of variables affecting the measurements may be reduced. By measuring the pressure gradient across two locations, factors such as drift may be less of a problem as compared to compared to conventional systems that measure the pressure gradient by referencing pressure measurements at each location to a vacuum. In addition, the combined left and right atrial information may be used to diagnose septal defects. In one embodiment, the information generated by the leads may be provided to an external monitoring or control system.

Figure 4A:
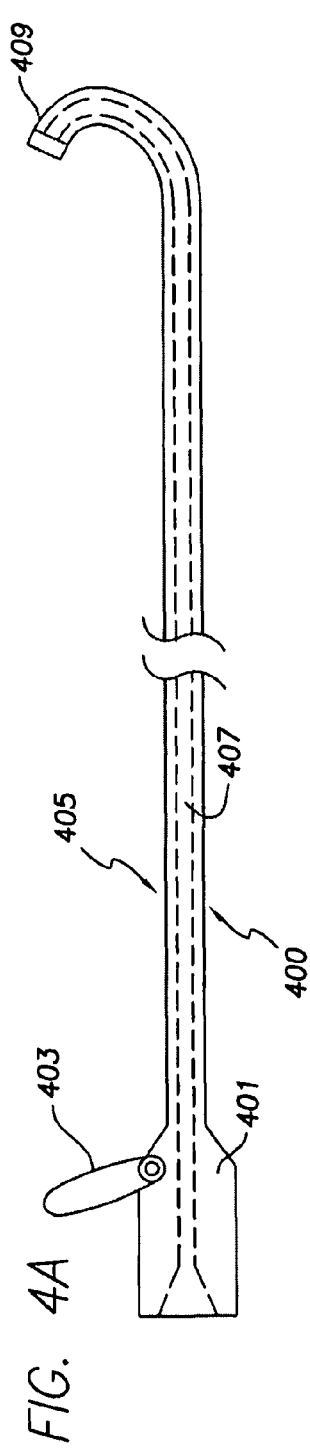
FIG. 4A is a diagram of one embodiment of a deflectable catheter.

FIG. 4A is a diagram of one embodiment of an introducer catheter 400 or sheath. In one embodiment, the introducer catheter 400 may have a proximal end with a housing 401. The catheter 400 may be formed of polyether block amide, high density polyethylene, silicone rubber, polyurethane or other materials. The materials used to form the catheter 400 may be biocompatible to prevent complication during insertion procedures.

In one embodiment, the housing 401 may be formed to couple to other devices or components. For example, the housing 401 may be formed to receive a dilator, needle or similar component. The proximal end of the catheter 400 may also include openings to a set of lumens 407 within the catheter 400. As used herein "set" refers to any number of items including one. The catheter 400 may contain any number of lumens. The lumens may run the length of the catheter or only run over a portion of the catheter 400. The lumens may include a primary lumen 407. The catheter may have a diameter large enough to allow insertion of other components such as a dilator, needles and leads. The diameter may be small enough to enter and traverse the vascular system of a patient. In one embodiment, the diameter of the catheter may be 1-10 mm. The primary lumen 407 may have a diameter sufficient to receive a lead, dilator, needle or other components.

In one embodiment, the catheter 400 may be a deflectable catheter. The catheter may be manipulated to curve at its distal end to facilitate insertion. In a further embodiment, the catheter may be precurved. The catheter 400 may include a main body 405. The main body 405 may have any length. In one embodiment, the main body 405 has sufficient length to traverse an intravenous path to the right atrium of a heart. The housing 401 may include a mechanism 403 to control the distal end of the catheter 400 as it is advanced into a patient. The mechanism 403 may be a lever 403, control stick, handle or other mechanism to control the curve of the distal end of the catheter 400 using a wire line system or similar system. The distal end may contain or be covered with a marker 409 to assist in the insertion process. The marker 409 may be a heavy metal such as tantalum or similar substance that is visible via fluoroscopy or other system for tracking instruments in a patient.

Figure 4B:
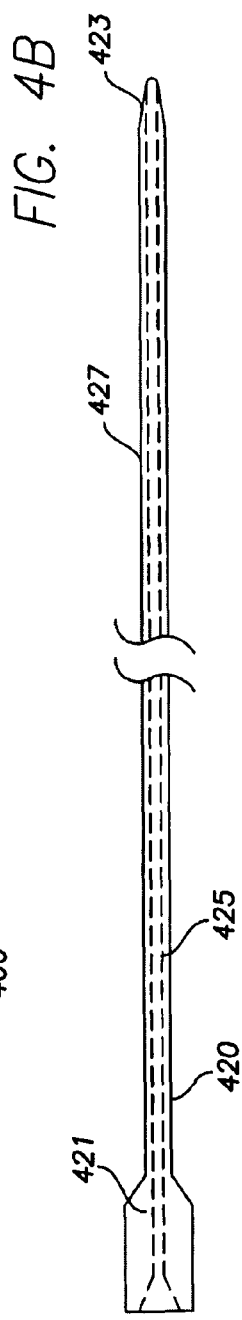
FIG. 4B is a diagram of one embodiment of a dilator.

FIG. 4B is a diagram of one embodiment of a dilator 420. The dilator 420 may have a housing 421 at the proximal end, a long tubular body 427 and a distal tip 423. The long tubular body may define an inner lumen 425. The inner lumen 425 and body 427 may be flexible to assist during insertion of the dilator. The dilator may be formed from silicon rubber, polyurethane, polyether block amide, high density polyethylene and other materials. The diameter of the dilator may be between 1-8 mm. In one embodiment, a portion of the dilator near the tip may have a larger outer diameter. In one embodiment, the length of the enlarged portion may be 5-8 mm. The length of a standard distal end 423 may be 1-5 mm.

Figure 4C:
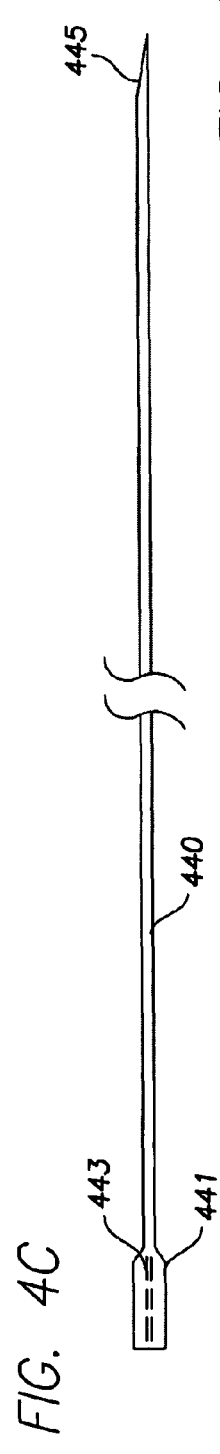
FIG. 4C is a diagram of one embodiment of a trans-septal needle.

FIG. 4C is a diagram of one embodiment of a needle 440. The needle 440 may have a proximal end 441 with an enlarged diameter. The proximal end 441 may be formed to be coupled to other instruments and devices. For example, the proximal end 441 may be coupled to a die injection device or similar device. The proximal end 441 may also include an opening to an interior lumen 443 or set of lumens. These lumens may run the entire length of the needle 440 or over a portion of the needle. The needle may be formed from a flexible material to allow it to follow the path of a dilator or catheter through a vascular system of a patient to the heart. In one embodiment, the needle 440 may be partially or fully formed from steel, Nitinol (an alloy of nickel and titanium), or another alloy or metal. The needle may have a diameter of 0.25 to 3 mm or any other suitable diameter.

In one embodiment, the distal end of the needle 440 may form a point 445. The point 445 may be sharp to puncture through organic structures. The end point 445 may also be open allowing access to the interior lumen. In another embodiment, the needle 440 may be solid with a solid tip 445.

Figure 4D:
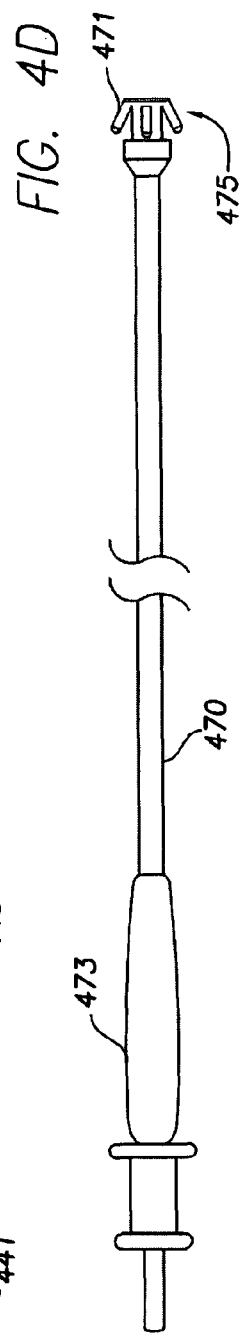
FIG. 4D is a diagram of one embodiment of a lead.

FIG. 4D is a diagram of one embodiment of a lead 470. The lead 470 may a flexible tube like structure with a diameter small enough to fit within a catheter. In one embodiment, the lead 470 may have a diameter between 1-10 mm. The lead 470 may be of any length. The lead 470 may have a length sufficient to reach the heart through a catheter inserted into a patient. The lead 470 may be primarily formed from polyurethane, silicone rubber, polyether block amide, high density polyethylene or other flexible biocompatible materials. In one embodiment, the lead 470 may be substantially formed from a single material.

In one embodiment, at a distal end the lead 470 includes a head portion 475. The head portion 475 may include a sensor 471. The sensor 471 may be attached through adhesive or similar chemical bonding, form fit, snap fit, welding or any other attachment mechanism. The sensor 471 may be a fluid pressure sensor or similar sensor type. Example sensor types are discussed in greater detail below. The sensor 471 may be utilized to monitor pressure in the left atrium. The distal end may also include a marker to allow monitoring of the position of the lead tip in the body of the patient. For example, the marker may be a heavy metal that is visible through fluoroscopy.

In one embodiment, the lead 470 includes a proximal housing 473. The proximal housing 473 may include an attachment mechanism. The attachment mechanism may allow the lead 470 to be attached to an implantable device.

In one embodiment, the lead 470 includes a set of lumens that may include a primary lumen (not shown) that provides a space for a set of electrical conductors to connect with the sensor 471. The primary lumen may run the length of the lead and have a proximal end that is in the form of a connector or that is coupled to an extension of the lumen in the proximal housing 473 that allows coupling to an implantable device. A set of electrical connectors may be present at the proximal end of the lumen. A male-female coupling attachment or similar attachment mechanism may be combined with the electrical connectors to enable the sensor 471 to be in electrical communication with an external device.

In one embodiment, various external monitoring or control devices may be coupled to the lead 470 at the proximal end. For example, devices may be attached for inserting or controlling other components in the lead 470 or for controlling the flow of fluid through the set of lumens in the lead 470. In another example, the external device may be a monitoring device that collects information from the lead sensor 471 and a stimulation device that generates an electrical pulse to stimulate the heart through an electrode implanted within the lead 470 or as part of the lead 470. In this example, the lead 470 may have a set of electrodes in the head portion or near the head portion that are in contact with the septal wall or other parts of the heart when the lead 470 is in place. This set of electrodes can be used to induce an electrical current or pulse to the heart for use in pacemaker and defibrillator type applications.

Figure 5:
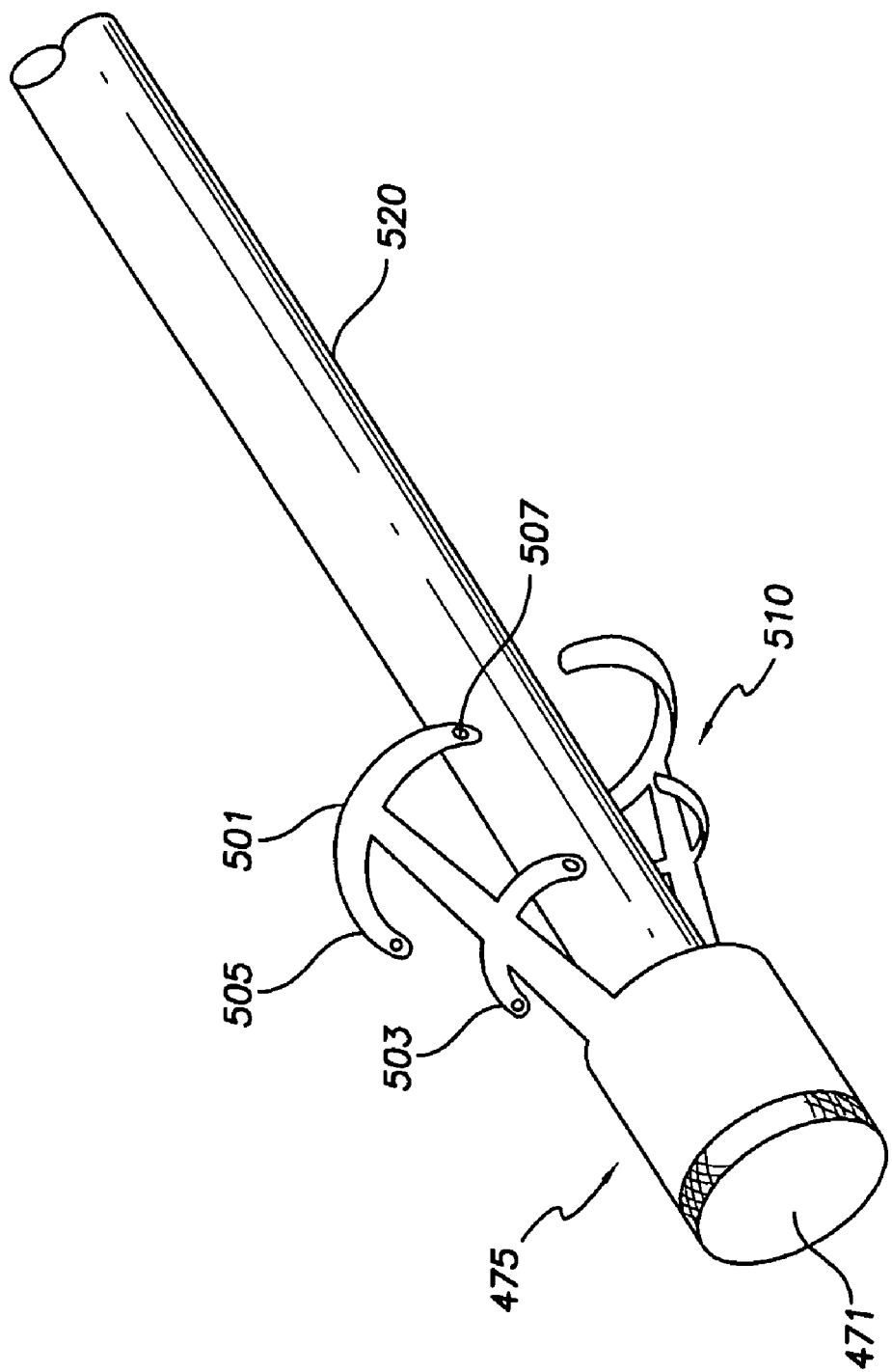
FIG. 5 is a diagram of one embodiment of a head portion of a lead.

FIG. 5 is a perspective view of one embodiment of the lead 470. The sensor 471 may be mounted in a distal end of the head portion 475. The sensor may have a circular, ovoid or other shape to fit through the primary lumen of the catheter and to fit through a passage formed in a septal wall of the heart by a needle. The head portion 475 may have a mounting mechanism 510 attached to the outer surface or integrally formed with the head portion 475.

In one embodiment, the mounting mechanism 510 includes a set of arms 501. The set of arms are flexibly attached to a proximal end of the head portion 475. Any number of arms may be a part of the mounting mechanism 510. In an example embodiment, two arms are present. Each arm may have a set of protrusions 503, 505. A first set of protrusions 503 may extend outward from the arm in a mid portion of the arm. A second set of protrusions 505 may extend outward from the arm at or near the end of the arm. The protrusions may have an arcuate or similar shape that is directed inward toward the body portion 520 of the lead. When compressed against the sides of the body portion the protrusions may wrap around the outer surface of the body portion 520. In another embodiment, the arms and protrusions may have other shapes that are squared, angular or similarly designed. In one embodiment, the protrusions may be angled toward one another to pinch or clamp down on a septal wall when deployed. In another embodiment, either the smaller or the larger set of protrusions is angled while the other set of protrusions are generally perpendicular to the arms.

In one embodiment, the set of arms may have a natural position extending slightly away from the body portion 520. In an example embodiment, each arm may have a material memory with a natural position that is angled away from the body 520 such that the end of each arm is 1-2 mm from the body portion 520. The base of each arm where the arm meets the head portion 475 may be flexible. The arms may bend away from the body portion to a position where the end of each arm is adjacent the sensor 471. In another embodiment, the arms may be hingedly attached, ball and socket attached or similarly attached to be moveable in relation to the head portion. In one embodiment, when folded back toward the sensor the arms may not have a biasing force. The outer casing of the head portion 475 and the set of arms 501 may be formed from polyether block amide, high density polyethylene, silicone rubber, polyurethane or other materials In one embodiment, marker materials 507 such as heavy metals including tantalum and platinum may be adhered or embedded into the arms and the protrusions. The marker materials 507 may be used in conjunction with a technology such as fluoroscopy to monitor the position of the arms to determine a position of the mounting mechanism and verify proper deployment.

Figure 6A:
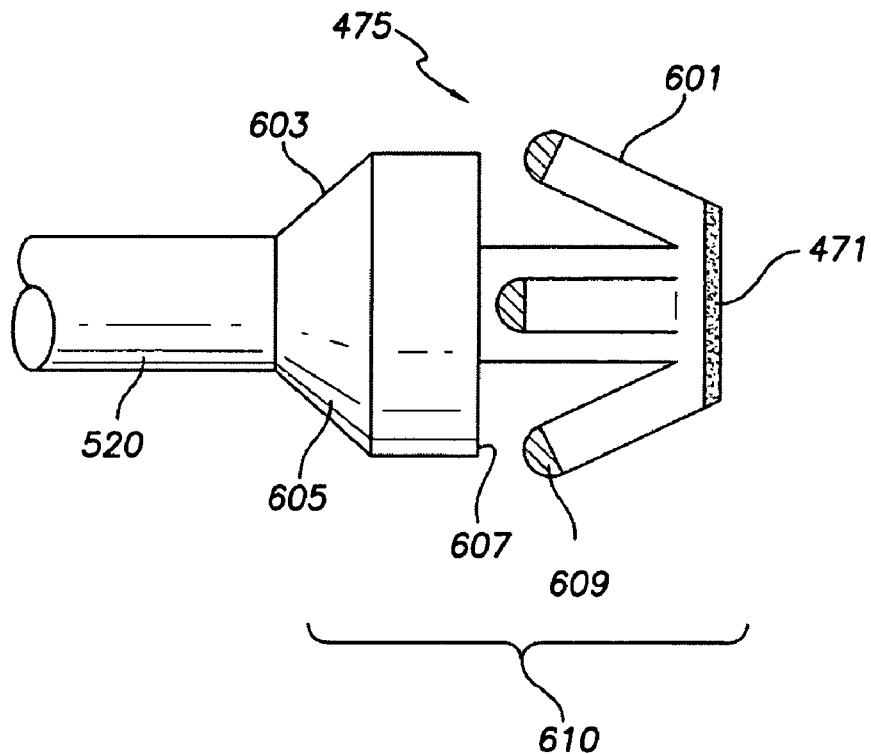
FIG. 6A is a diagram of one embodiment of a head portion of a lead.

FIG. 6A is a diagram of one embodiment of the lead. The lead includes a mounting mechanism 610. The mounting mechanism includes a proximal anchor 607 and a distal anchor 601. The two anchors work together to clamp a septal wall between them to hold the head portion 475 in place.

The proximal anchor 605 may be a wide section of the head portion 475. In one embodiment, the proximal anchor 605 may have a diameter roughly exceeding that of the sensor 471 in the head portion 475. The proximal anchor 605 provides a surface against which the distal anchor presses the septal wall. The proximal anchor 605 includes a tapered portion 603 and a squared flat portion 607. The tapered portion 603 connects the proximal anchor with the body portion 520. The tapered portion 605 allows the head portion 475 to be retracted partially through a septal wall to a secured position. The tapered portion 605 gently pushes the hole in the septal wall wider without permanently widening the hole. The squared flat portion 607 of the head portion 475 provides a surface against which the septal wall may abut or be pressed to hold the head portion 475 in place. The squared flat portion 607 may be a surface that is roughly perpendicular to the tubular mid section of the head portion 475. The squared flat portion 607 may have a width of 0.25 mm to 4 mm to provide a surface onto which the septal wall may be pressed to clamp the septal wall in place in relation to the head portion 475. The mid section of the head portion 475 is narrower than the proximal anchor. When in place the septal wall will surround this area of the head portion 475.

The distal anchor 601 may be a set of tines. The head portion 475 may have a set of extending tines 601 attached near the distal end. The tines 601 may be pressed against the head portion 475, for example when inserted into the catheter, so that the outward protrusion of the tines 601 is less than that of the proximal anchor 605. Any number of tines 601 may be provided. In one embodiment, three or more tines 601 are provided. The tines 601 may be equally spaced and provide a footprint to press against a septal wall. In some embodiments, the tines 601 are positioned a given distance apart on the tip. When in the extended position pressing, the tines 601 maybe spaced apart at their base from the anchor 605 at a distance approximately equal to the thickness of the septal wall in the area of the implant. For example, the distance may be 3-4 mm.

Figure 6B:
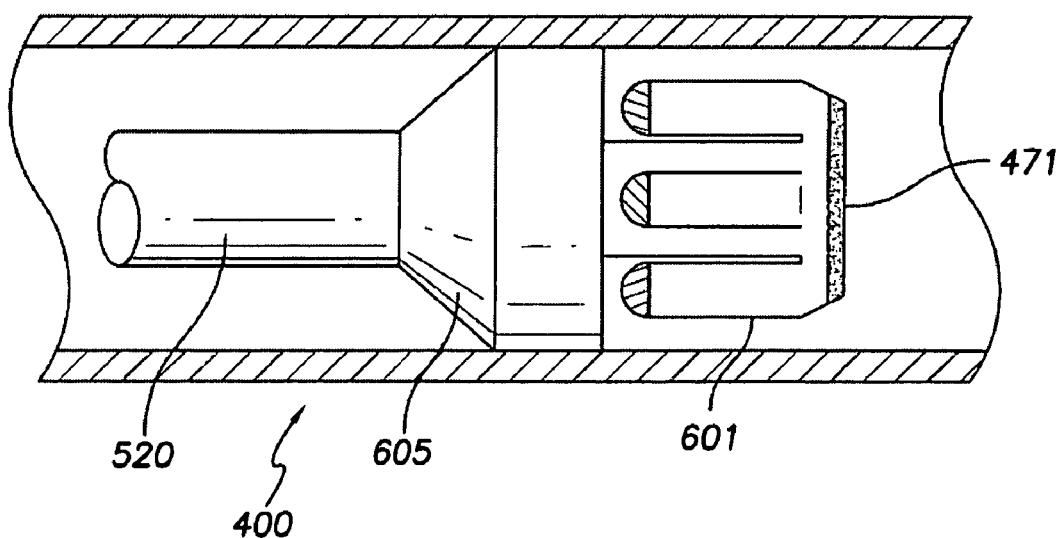
FIG. 6B is a diagram of one embodiment of a head portion of a lead in a catheter.

In one embodiment, the tines 601 may be flat strips of metal, metal alloy, silicone, polyurethane, plastic or similar resilient materials. In another embodiment, the tines 601 may be formed from biodegradable material. This type of material may be used, for example, in a case where it may be necessary to remove the lead after implantation. The tines 601 may fold against the body of the mid section of the head portion 475 during insertion into the patient through the catheter 400, as depicted in FIG. 6B. The tines 601 may expand in the left atrium of the heart after the mid section of the head portion 475 passes through the catheter and the hole in the septal wall. The space between the base of the tines 601 and the proximal anchor 605 may be small enough to press against each side of the septal wall once inserted through the septal wall. The space between the base of the tines 601 and the proximal anchor 605 in its natural position may be slightly smaller than the typical thickness of the septal wall or fossa ovalis.

In one embodiment, the set of tines 601 may have marker material 609 attached to them or imbedded in them. The marker material 609 may be a heavy material such tantalum or platinum that can be detected through fluoroscopy.

Figure 7:
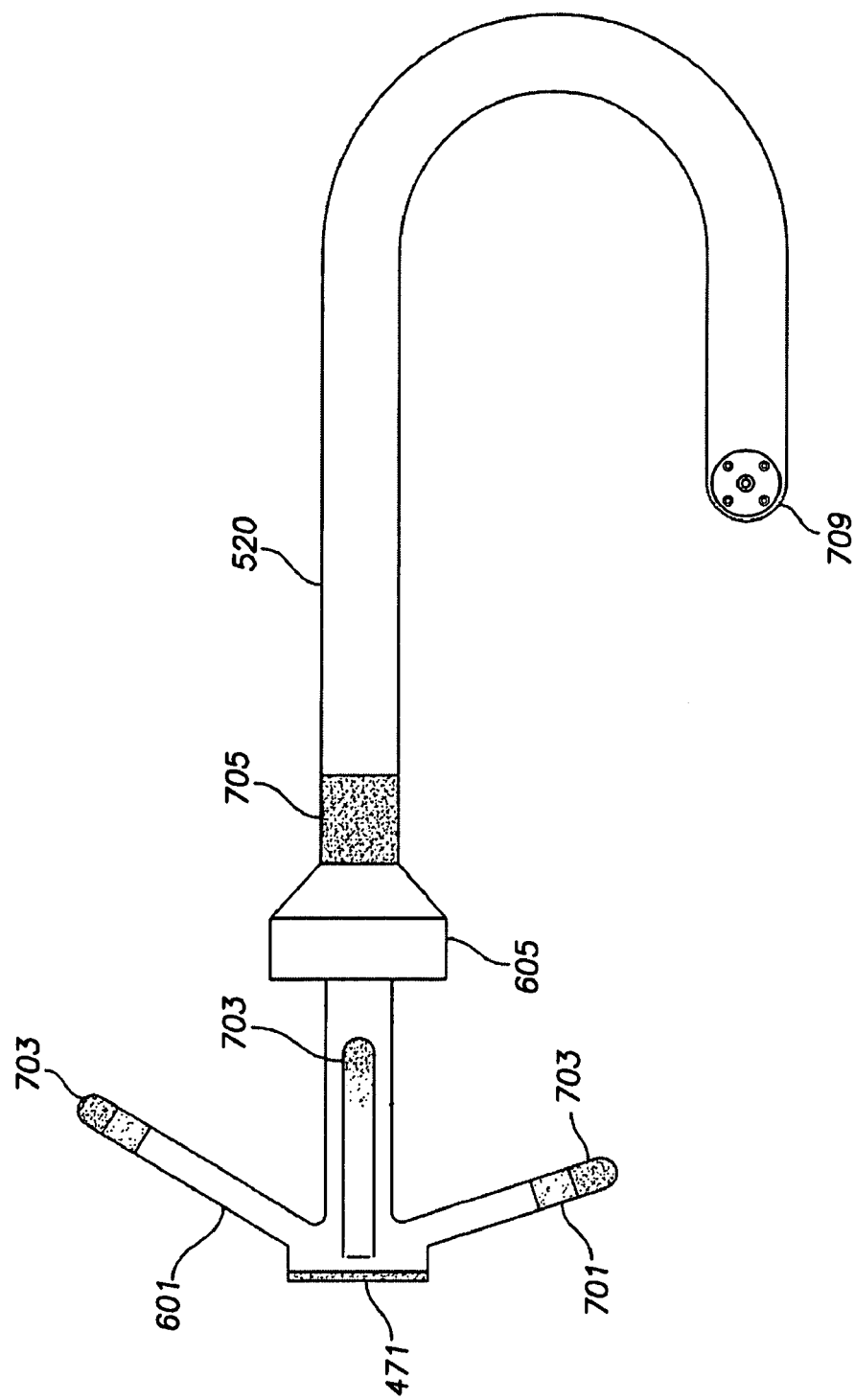
FIG. 7 is a diagram of one embodiment of a head portion of a lead.

FIG. 7 is a diagram of one embodiment of a lead. The lead includes a set of tines 601 as a distal anchor, a proximal anchor 605 and a body portion defining a set of lumens for a set of conductors such as wires 709. The wires 609 may include a conductor coil and similar cables. The tines 601 may include a set of electrodes 703 on the tip of each tine 601 or on the tip of at least one tine. The electrodes may be used to apply an electrical signal to the septal wall and the heart when in place. The electrical signal may be carried by the conductor coil or similar conducting medium. The electrical signals applied by the electrodes may be used for pacing, defibrillation or similar therapy. In one embodiment, the electrodes are cathode electrodes. In one embodiment, the electrodes in each tine 601 may be separately controlled and wired or any combination of the electrodes 703 may be wired or controlled together or separately.

In one embodiment, the tines 601 may also include a medicating sleeve 701 or be composed of materials impregnated with medication. This sleeve or impregnated material may contain medication or similar chemicals to be introduced into the heart, applied to the septal wall or placed in the bloodstream when the lead is in place. In one embodiment, the medicating sleeve or material may be a silicone rubber, polyurethane or similar biocompatible materials impregnated with the medication. The medication may be in a powder form that is mixed with the material to form a ring, sleeve or similar structure to be placed on the structures of the head portion 475 of the lead or used in the materials for the structures of the head portion 475 of the lead. The medication or chemical in the sleeve may be time released, contact released or released through a similar mechanism. In one embodiment, the sleeves may be impregnated with anti-inflammatory agents such as various types of steroid. The introduction of the anti-inflammatory agent may be used to hasten the healing around the hole in the septal wall or the build up of intima.

In one embodiment, an electrode 705 may be placed at the distal end of the body portion 520 adjacent the proximal anchor 605. The electrode 705 may be used to apply, via a wire 709, an electrical current to the heart for purposes of pacing or defibrillation. The electrode 705 may work in conjunction with the electrodes 703 in the tines 601. In one embodiment, the electrode 705 is an anode electrode.

FIG. 8 is a diagram of one embodiment of a head portion 475, mounting mechanism and sensor 471 of a lead. In one embodiment, the mounting mechanism includes a set of tines 601 and a proximal anchor 605 housing a biasing mechanism such as a spring 603 (shown in a partial cut-out view). The spring 803 is housed in an interior compartment of the proximal anchor 605. The interior compartment is annular in shape. The outer walls of the annular compartment and lead are flexible. The distal end of the proximal anchor also has a stiff circular or ovoid section 801 that forms an end cap for proximal anchor 605 and its interior compartment. The end section 801 slides in relation to an inner core of the lead. If pressure is applied to the end section 801, the end section 801 slides in a proximal direction compressing the spring 803 and flexing the outer walls of the proximal anchor 605. In one embodiment, the end section 801 may be an electrode for applying (e.g., via a wire 709) an electrical signal to the heart.

The electrode may be used for applying therapy in the form of pacing signals or defibrillation. In one embodiment, the electrode is a cathode electrode.

In one embodiment, the inner core extends beyond the proximal anchor 605 of the lead and houses the sensor 471. The extended section of the inner core may also have a set of extending tines 601 attached near the tip. Any number of tines 601 may be provided. In one embodiment, three or more tines 601 are provided. The tines 601 may be equally spaced and provide a footprint to press against a septal wall. In some embodiments, the tines 601 are positioned a given distance apart on the tip. The base of the tines 601 may be spaced apart from the base of the anchor 605 at a distance approximately equal to the thickness of the septal wall in the area of the implant. For example, the distance apart may be 3-4 mm.

In one embodiment, the spring mechanism 803 may maintain the pressure on the septal wall and pull the tines 601 flat against the septal wall to maintain a low profile for the tines 601 and sensor 471. The spring mechanism 803 may be a metal spring or spring made from other materials with strong material memory. The spring may be MP35N, nickel chrome alloys or other biocompatible materials. In another embodiment, a separate spring structure may not be present. The outer walls of the proximal anchor 605 may be formed with materials or a structure with a memory and resiliency equivalent to a separate spring structure. The outer walls may thus function as a spring to pull the tines 601 into place when deployed.

In one embodiment, the body portion may include an electrode 705. This electrode 705 may work separately or in conjunction with the end portion electrode 801 to administer electrical signals to the heart for therapeutic purposes such as pacing or defibrillation. In one embodiment, the body portion electrode 705 is an anode electrode.

In one embodiment, the tines 601 may include a marker material 609 that is attached or embedded into the tines 601. The marker material may be a heavy metal such as tantalum or platinum that may be detected by fluoroscopy.

FIG. 9 is a diagram of one embodiment of a head portion of a lead. This example head portion may have similar characteristics to the embodiment of FIG. 8 including the end portion electrode 801 and body portion electrode 805. In addition, the example embodiment may include an impregnated section or sleeve 909 containing medication. This medicating section or sleeve may be used to introduce medication, chemicals or other substances into the heart or the blood stream. The medicated sleeve or section may time release the therapeutic element or release the therapeutic element on contact or through a similar release mechanism. The sleeve or section may be located on the exterior or interior of the proximal anchor portion 605. In one embodiment, the sleeve or section is a silicone sleeve or similar structure impregnated with an anti-inflammatory agent such as a steroid.

FIG. 10A is a diagram of one embodiment of the head portion of the lead. In this embodiment, the head portion 475 includes a first set of tines 601 and a second set of tines 1001 acting as the proximal anchor. The second set of tines 1001 also collapses against the wall of the head portion 475 to allow the head portion 475 to be inserted into a catheter and into the left atrium of the heart. The second set of tines 1001 may also collapse when retracted through a hole in a septal wall to place the head portion 475 in a secure position. The first set of tines 601 may include any number of tines, including two or more tines. The second set of tines 1001 may include any number of tines, including two or more tines.

In one embodiment, the second set of tines 1001 may include a set of electrodes 1005 and medicated sleeves or sections 1003. The set of electrodes 1005 may be utilized to apply an electrical signal from an external device to the heart for therapeutic purposes. The electrodes 1005 may be used for pacing, defibrillation or similar therapeutic use. In one embodiment, the set of electrodes 1005 may be cathode electrodes. The set of electrodes 1005 may each be separately wired and controlled or wired and controlled in any combination. A second electrode 1007 may be located in a body portion adjacent the head portion 475. This electrode 1007 may function independent of the other electrodes 1005 or in conjunction with the other electrodes 1005 to administer electrical signals to the heart for pacing, defibrillation or similar therapeutic purposes. In one embodiment, the second electrode 1007 is an anode electrode.

In one embodiment, the medicated sleeves 1003 may be used to introduce medication, chemicals or similar substances into the heart. In one embodiment, the medicated sleeves or sections 1003 may be time released, contact released or similarly released medication or similar substances. In one embodiment, the sleeves or sections 1003 are silicone impregnated with anti-inflammatory agents such as steroids.

FIG. 11 is a diagram of one embodiment of a head portion of a lead. The head portion 475 includes a distal anchor in the form of a set of tines 601 and a proximal anchor 605. Between the distal anchor and proximal anchor 605 is an electrode 1103. The electrode 1103 may be used to apply an electrical signal to the septal wall of the heart for therapeutic uses such as pacing and defibrillation. In one embodiment, the electrode 1103 may be a cathode electrode. A second electrode 1105 may be present on the body portion of the lead adjacent to the head portion 475. The second electrode 1105 may work independent of or in conjunction with the first electrode to provide therapeutic electrical signals for pacing, defibrillation or similar purposes. In one embodiment, the second electrode 1105 may be an anode electrode.

In one embodiment, the head portion 475 includes one or more medicating sleeves or sections 1101. The medicating sleeve or section 1101 may contain any type of medication, chemical or similar substance. In one embodiment, the medicating sleeve or section may be an impregnated silicone sleeve containing an anti-inflammatory agent such as a steroid. Medication or similar chemicals may be time released, contact released or similarly released.

A variety of tines or tine like structures may be used in embodiments of the mounting mechanism. For example, any number of tines or tine like protrusions may be used in each set of tines discussed herein. The tines may be configured to be extendable and retractable. The tines may have a retracted or compressed position that fits within a catheter. In one embodiment, the tines may also be electrically connected and function as electrodes to deliver electrical pulses to the septal wall.

Figure 12:
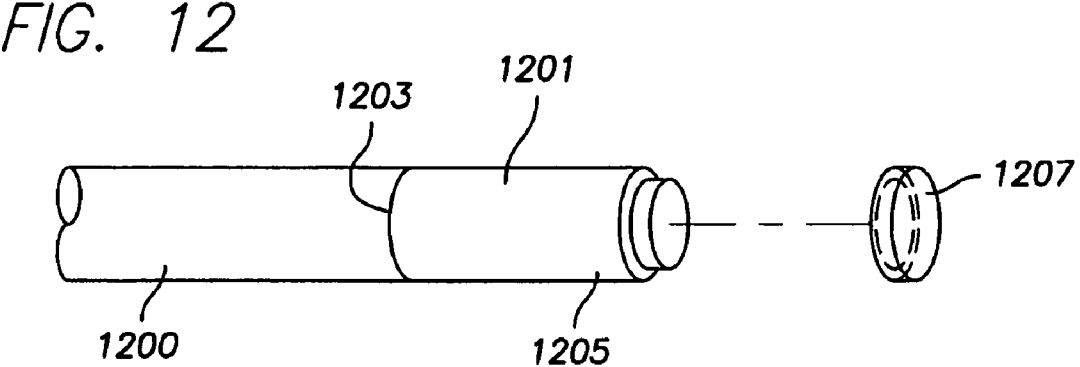
FIG. 12 is a diagram of one embodiment of a sensor attached to an end of the lead.

FIG. 12 depicts one embodiment of a sensor mounted on the distal end of a lead 1200. In this example, a sensor 1201 is attached to a distal end of a head portion 1203 of lead 1200. Typically, the sensor 1201 and the head portion 1203 would have the same diameter. Thus, they may be configured in a co-circumferential orientation. The sensor 1201 may be attached to the head portion 1203 by a variety of techniques including, for example, laser welding and adhesive attachment (e.g., using an epoxy).

In one embodiment, the sensor 1201 may include a flexible diaphragm 1207 at its distal end. The sensor case 1205 and flexible diaphragm 1207 are shown in an exploded view to illustrate one technique for attaching the flexible diaphragm 1207 to the sensor case 1205. Specifically, the flexible diaphragm 1207 may be formed with a lip that is placed over a seat provided on the end of the sensor case 1205. Thus, an inside surface of the lip may, for example, be adhered to an outside surface of the seat. The lip of the flexible diaphragm 1207 may be attached to the seat of the sensor body using a variety of techniques including, for example, laser welding and adhesive attachment (e.g., using an epoxy).

In general, various aspects of the sensor may be constructed using known materials and techniques. For example, the sensor case may be constructed of a variety of materials including, for example, titanium or other biocompatible metals and materials. The sensor may include a pressure-to-electrical transducer such as a piezo electric chip. One or more electrical conductors may be routed out the proximal end of the sensor 1201 through the lead 1200 to connect the sensor 1201 to an external device (not shown).

The case 1201 interior may be filled with a biocompatible fluid or gel such as, for example, silicone oil. A port may be provided in the sensor case to facilitate filling the interior with fluid and for removing bubbles from the fluid. A plug mechanism such as a screw may be used to close the port.

Figure 13:
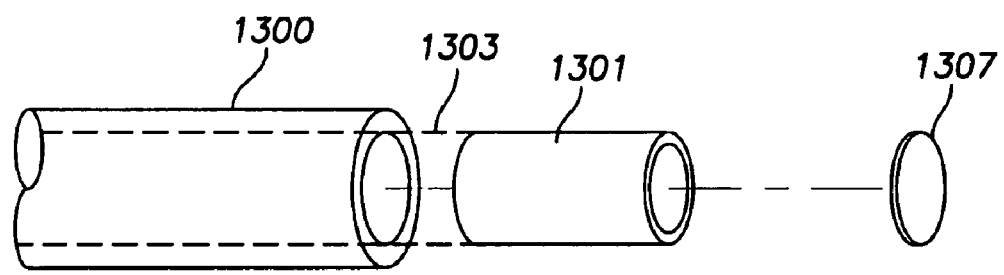
FIG. 13 is a diagram of one embodiment of a sensor attached to the lead internally.

FIG. 13 depicts an embodiment of a lead 1300 where a sensor 1301 is inserted into a distal end of a head portion 1303 of the lead 1300. The sensor 1301 includes a flexible diaphragm 1307 on its distal end. The lead body 1303 and sensor 1301 are shown in an exploded view to illustrate how these components may be assembled.

In one embodiment, the sensor 1301 is inserted into the head portion 1303. In this case, an outside surface of the sensor 1301 may be affixed to an inside surface of the head portion 1303. Typically, the sensor 1301 will be fully inserted into the head portion 1303. Thus, the distal ends of the head portion 1303 and the sensor 1301 (e.g., the flexible diaphragm 1307) may be aligned. In this case, the mounting mechanism (not shown) may be attached to or built into the head portion 1303.

Figure 14:
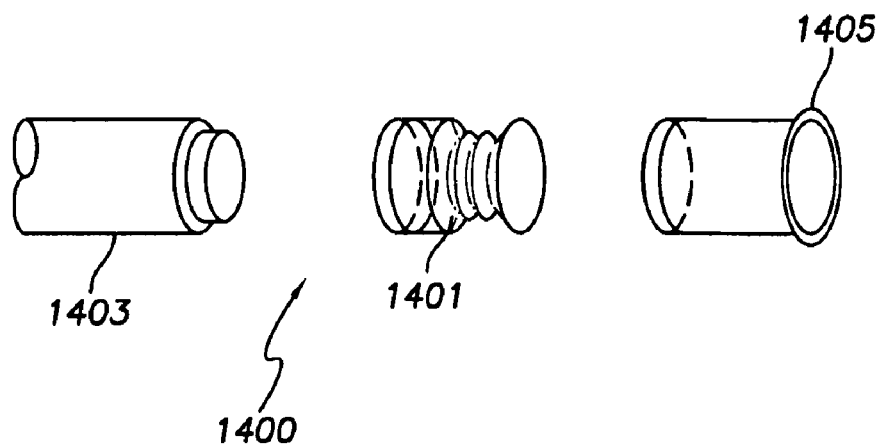
FIG. 14 is a diagram of one embodiment of the components of the sensor.

FIG. 14 depicts one embodiment of an exploded view of one embodiment of a sensor 1400 incorporating a flexible bellow 1401. A main sensor housing 1403 incorporates a pressure-to-electrical transducer that generates electrical signals provided to an electrical conductor.

The main sensor housing 1403 also includes a seat adapted to receive a base portion of the bellow 1401. An inside surface of the base portion may, for example, be adhered to an outside surface of the seat using a variety of techniques including, for example, laser welding and adhesive attachment (e.g., using an epoxy).

The distal end of the bellow comprises a wall or end piece that forms the distal end of the sensor assembly 1400. The interior of the bellow 1401 and the main housing 1403 may then be filled with a non-compressible fluid.

In some embodiments, the sensor 1400 may include a bellow cover 1405. The bellow cover 1405 may facilitate attaching the sensor 1400 to a lead. For example, a mounting mechanism such as tines may be affixed to the outside of the bellow cover 1405. In addition, the bellow cover 1405 may include a lip to which a mounting mechanism such as a flexible membrane or balloon may be attached.

A base portion of the bellow cover 1405 may be adapted to be affixed to the base portion of the bellow 1401. An inside surface of the base portion of the bellow cover 1405 may, for example, be adhered to an outside surface of the base using a variety of techniques including, for example, laser welding and adhesive attachment (e.g., using an epoxy).

In operation, changes in pressure in the left side of the heart will cause a distal surface of a bellow 1401 in the sensor 1400 to move. In general, the bellow 1401 may expand and contract in relation to the fluid pressure.

Figure 15:
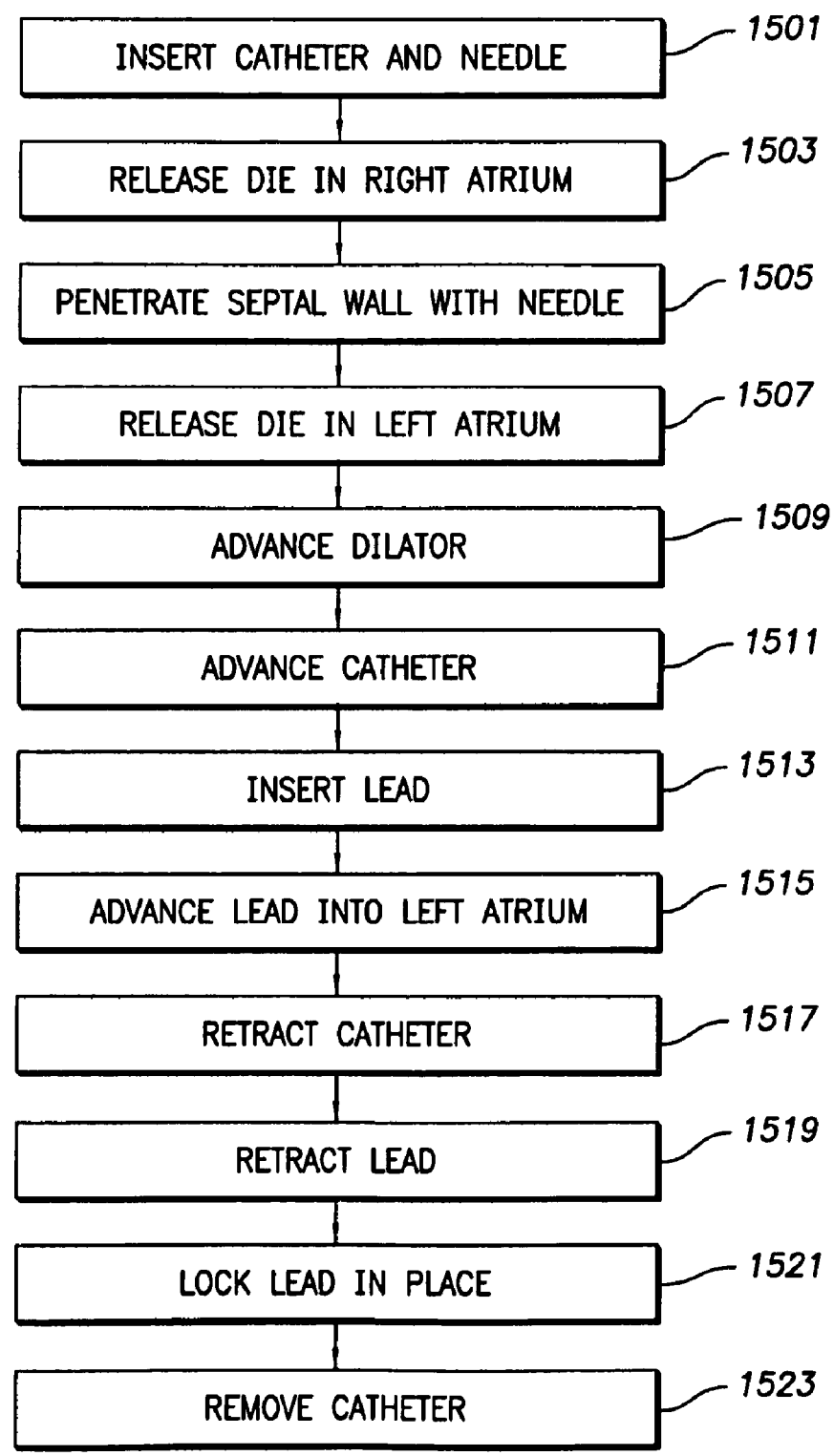
FIG. 15 is a flowchart of one embodiment of the process for inserting a lead.

FIG. 15 is a flowchart of one embodiment of a process for installing a lead and pressure sensor in the left atrium of the heart to monitor pressure in the left atrium. FIGS. 16-28 illustrate the process and will be referred to as part of the discussion of the process.

In one embodiment, the process of implanting the sensor begins by the placement of the catheter into the patient. The distal end of the catheter is placed into the right atrium of the patient using known techniques. The distal end of the catheter may be positioned adjacent the septal wall and the fossa ovalis. In one embodiment, after the catheter is in position a needle may be inserted into the catheter (block 1501). In another embodiment, the needle may be inserted along with a dilator with the needle extending past the end of the dilator.

In one embodiment, once the needle is in place with the distal tip of the needle in the right atrium a die may be released to detect or confirm the location in the heart of the catheter and needle (block 1503). The die may be used in connection with fluoroscopy or similar techniques and systems for monitoring instrument position in the body of a patient.

In one embodiment, with the location of the needle known in the right atrium, the needle may be repositioned, if necessary, and advanced to penetrate the septal wall at the fossa ovalis (block 1505). The release of die or other markers may continue through the process of penetration or may be restarted just after penetration of the septal wall (block 1507). The release of the die allows for confirmation of the penetration of the septal wall through fluoroscopy or similar systems. Also, the die released in the right atrium prior to penetration will flow through the puncture and indicate that the septal wall has been penetrated.

Figure 16:
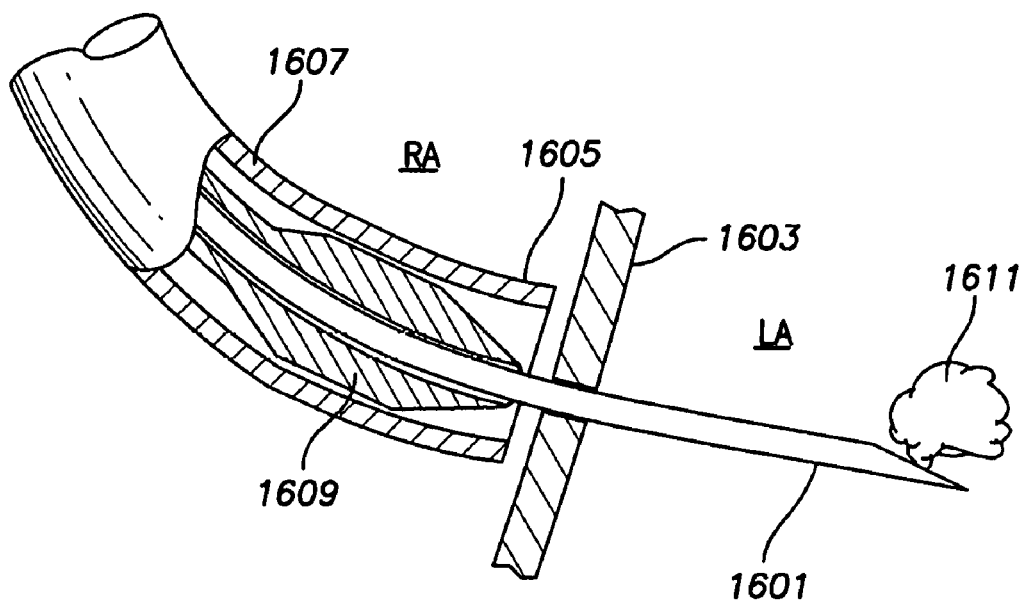
FIG. 16 is an illustration of a transeptal needle piercing a septal wall.

FIG. 16 is a diagram illustrating the penetration of the septal wall 1603 by a needle 1601. The needle 1601 has been advanced through the septal wall 1603. The position of the catheter 1607 in the right atrium ("RA") may be tracked by the marker tip 1605. At this point the dilator 1609 remains within the catheter 1607 until the penetration of the septal wall 1603 is confirmed by detecting the die 1611 in the left atrium ("LA"). In one embodiment, the dilator 1609 may have a tapered end and an enlarged portion that has a larger diameter than the main body of the dilator.

Figure 17:
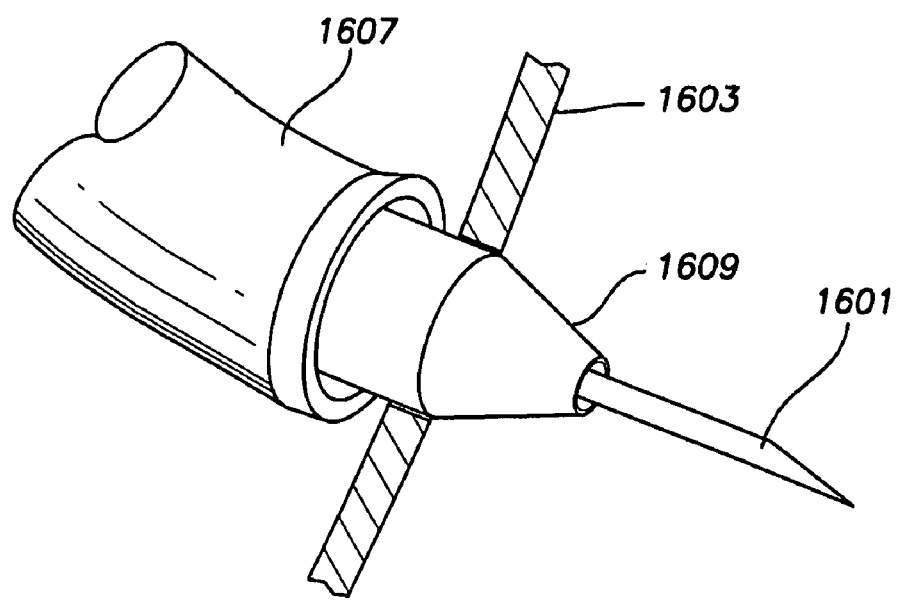
FIG. 17 is an illustration of a dilator enlarging a hole in a septal wall.

In one embodiment, after it has been confirmed that the needle successfully penetrated the septal wall, the dilator may be advanced through the opening created by the needle (block 1509). FIG. 17 is a diagram illustrating the advancement of the dilator 1609. The needle 1601 remains in place to guide the advancement of the dilator 1609. In one embodiment, the enlarged head of the dilator 1609 may be advanced to enlarge the hole in the septal wall and lodge the dilator in the hole. In another embodiment, the enlarged portion of the dilator 1609 may be advanced through the hole in the septal wall 1603 to enlarge the hole in the wall.

In one embodiment, after it has been confirmed that the needle successfully penetrated the septal wall, the catheter may be advanced into the opening created by the needle (block 1511). The needle and dilator may remain in place to guide the advancement of the catheter. In one embodiment, the distal end of the catheter may be advanced to enlarge the hole in the septal wall and lodge the catheter in the hole. In one embodiment, after the catheter is in place the needle and dilator may be removed from the patient and from the catheter. The catheter may maintain its position if a moderate pulling force is applied, but can be removed without damaging the septal wall.

Figure 18:
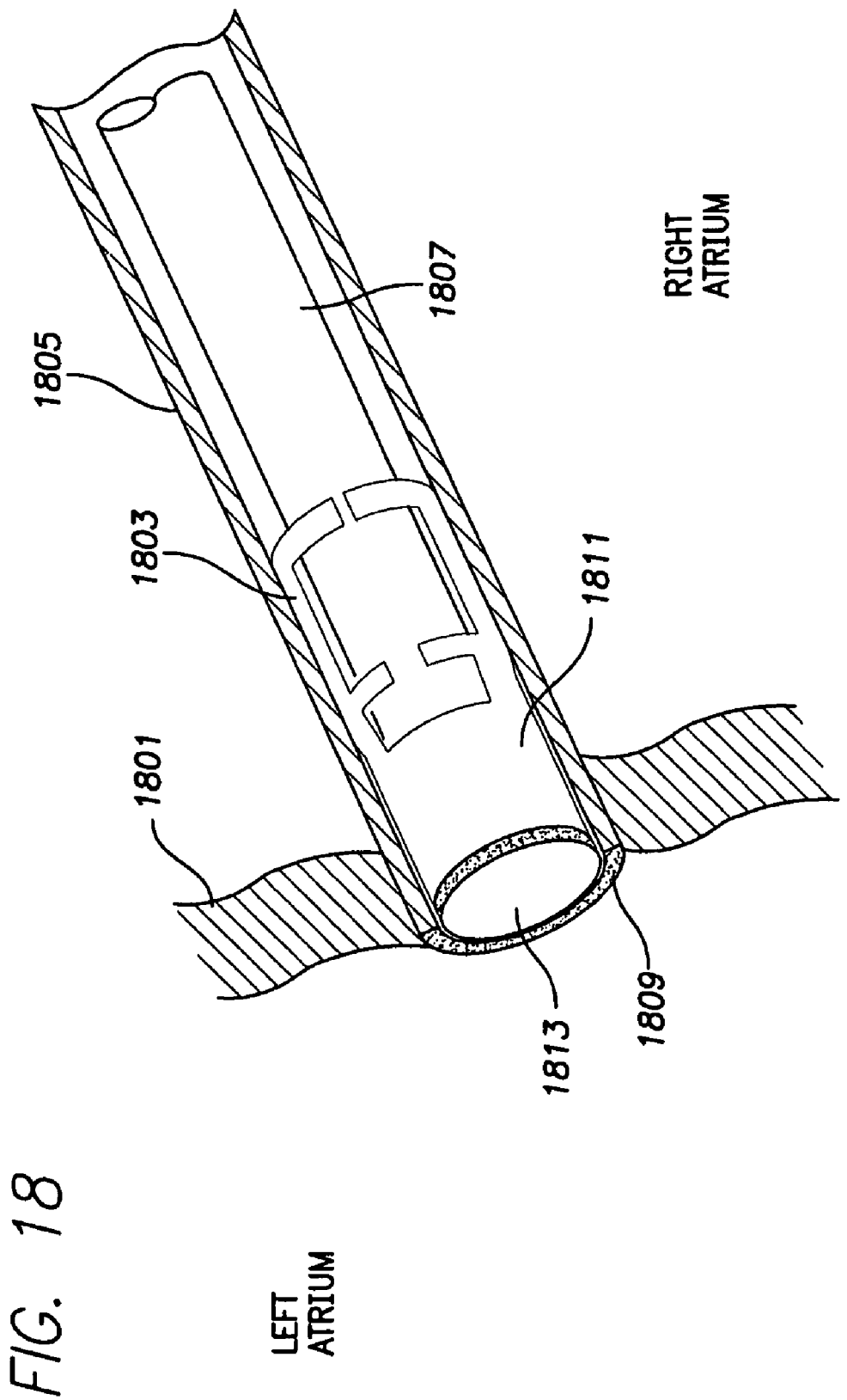
FIG. 18 is an illustration of one embodiment of a catheter and lead disposed through a septal wall.
Figure 22:
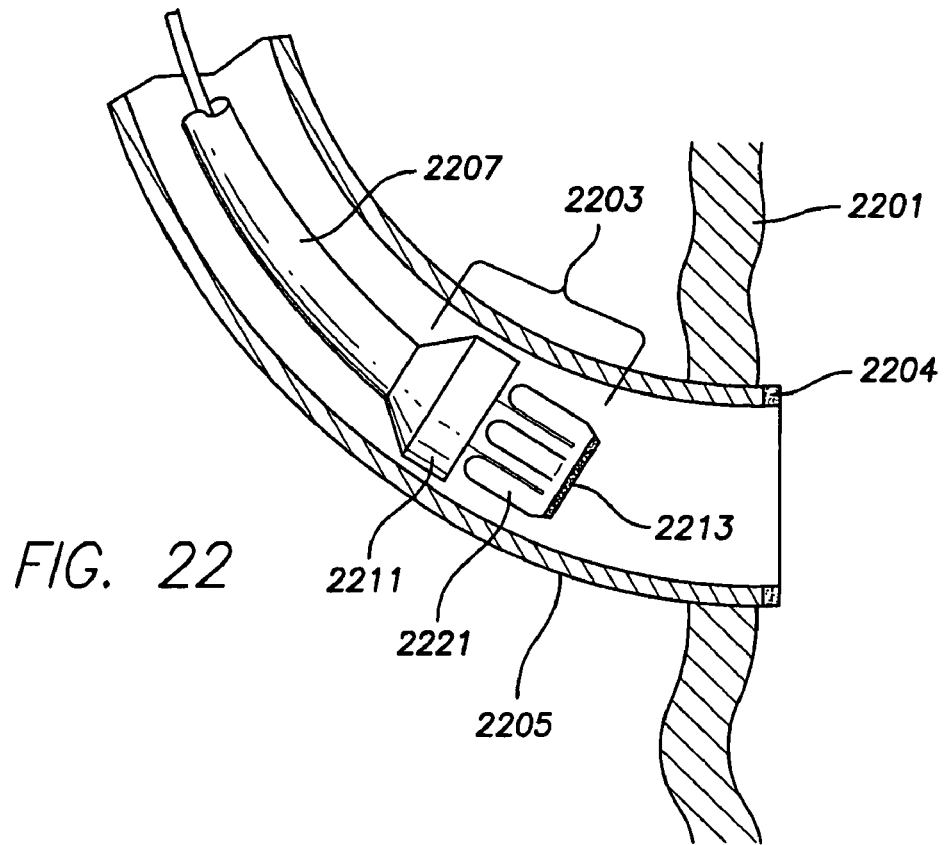
FIG. 22 is an illustration of one embodiment of a head portion of a lead inserted through a septal wall.

In one embodiment, after the needle and the dilator have been removed, the lead may be inserted into the patient (block 1513). The lead may be threaded through the catheter to lead it to the hole in the septal wall where the sensor at the tip of the lead is to be inserted. FIGS. 18 and 22 illustrate the advancement of the lead through the catheter. Referring to the FIG. 18, the distal tip of the catheter 1805 including a tip portion that may include a marker material for detection through fluoroscopy is lodged in the septal wall 1801. The lead is advanced through the catheter 1805 toward the distal end 1809. The distal end of the lead may include a sensor 1813 in the tip of the head portion 1811. The head portion may include a mounting mechanism 1803. The mounting mechanism 1803 may be collapsed to facilitate movement of the lead into a position at the distal end of the catheter in the left atrium of the heart. The head portion 1811 may be connected to a body portion 1807 that contains a lumen for housing wires and similar structures for connecting the sensor 1813 with external devices.

Referring to FIG. 22, this embodiment is similar to the embodiment of FIG. 18 except that a different mounting mechanism 2203 is utilized. The mounting mechanism 2203 includes a proximal anchor and distal anchor. The distal anchor may be in the form of a set of tines. The mounting mechanism 2203 may be a part of the head portion 2211 of the lead. The head portion 2211 may house a sensor 2213 and be connected to the body portion 2207. The lead may be advanced toward the distal tip 2209 of the catheter 2205, which is lodged in the septal wall 2201.

Figure 19:
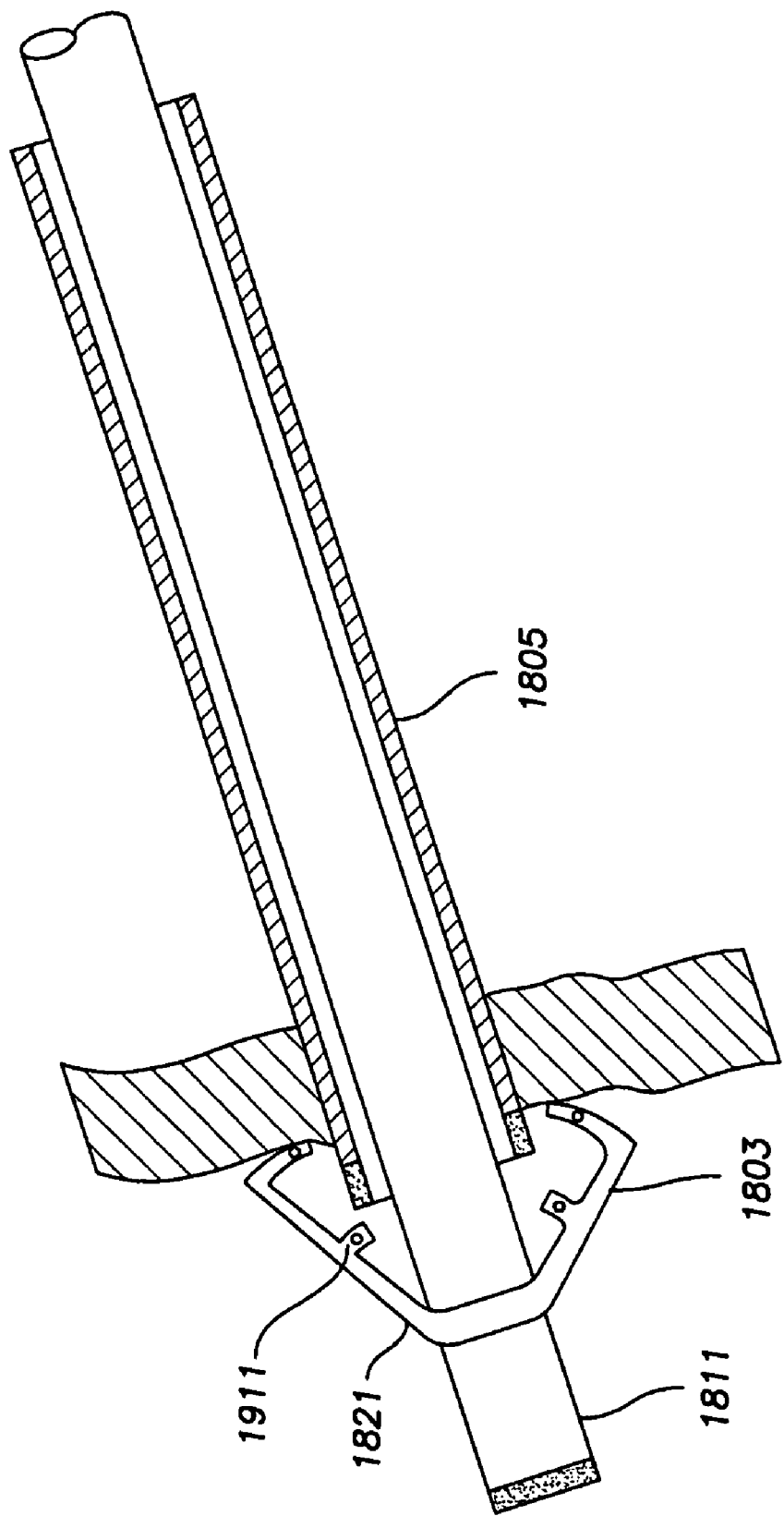
FIG. 19 is an illustration of one embodiment of a head portion of a lead disposed in a left atrium.
Figure 23:
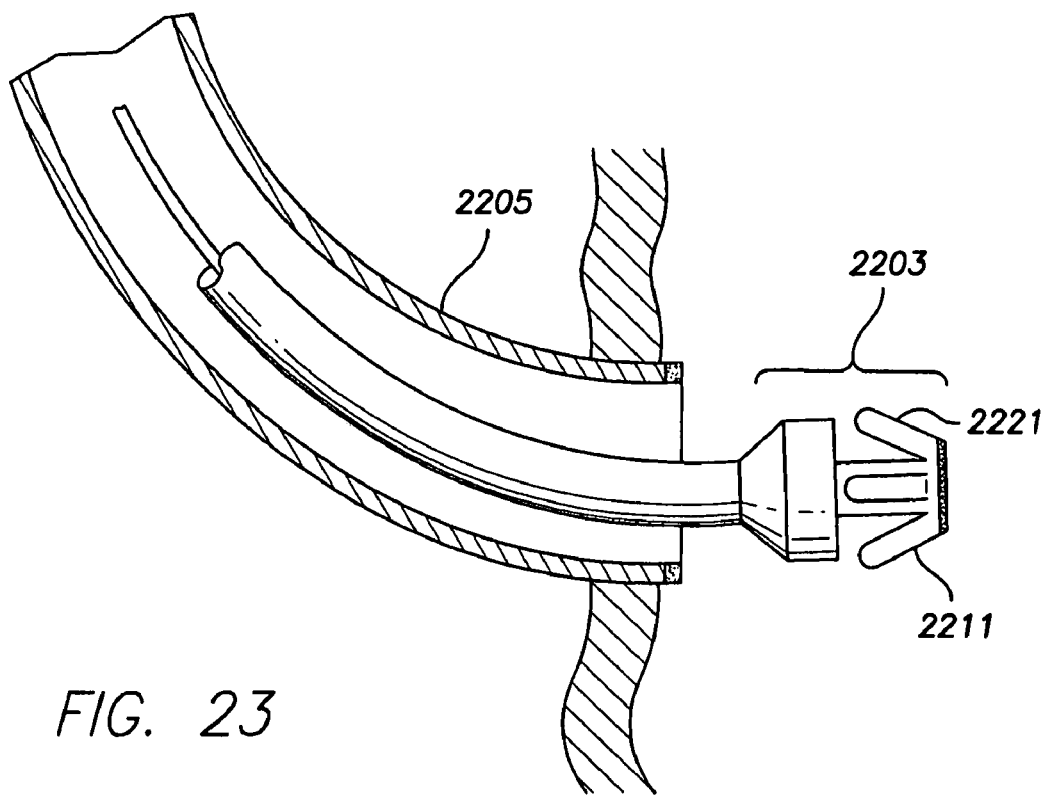
FIG. 23 is an illustration of one embodiment of a head portion of a lead disposed in a left atrium.

In one embodiment, the advancement of the lead continues until the head portion of the lead is partially or completely in the left atrium of the heart (block 1515). FIGS. 19 and 23 are diagrams illustrating the position of two embodiments, where the head portion has been advanced into the left atrium. In one embodiment, the head portion 1811, 2211 clears the distal end of the catheter 1805, 2205. After clearing the end of the catheter 1805, 2205 portions of the mounting structure 1803, 2203 may return to a natural position inhibited by the internal space of the catheter 1805, 2205.

Referring to FIG. 19, in one embodiment, a set of arms 1821 moves to a position based on the natural material memory of the arms 1821 and head portion 1811. The natural position may place the ends of the arms 1-5 mm from the outer surface of the head portion 1811 or body portion of the lead. In one embodiment, the position of the arms may be monitored through fluoroscopy by detecting the markers 1911 on or embedded in the arms.

Similarly, referring to FIG. 23, in one embodiment, a set of tines 2221 in a mounting mechanism 2203 may expand to a natural position of 1-5 mm at the end of each tine from the core of the head portion 2211 and the outer layer of the head portion 2211.

In one embodiment, after the head portion of the lead has been inserted into the left atrium the catheter may be retracted (block 1517). The catheter may be completely withdrawn or partially retracted. The catheter may be removed from the patient leaving the lead in place. The catheter may be a peelable catheter allowing the catheter to be easily removed without disturbing the lead and its connections. In one embodiment, the catheter may have a weakened area or wick along the length of the catheter to facilitate its removal. In another embodiment, the catheter may be cut off or similarly separated from the lead.

Figure 20:
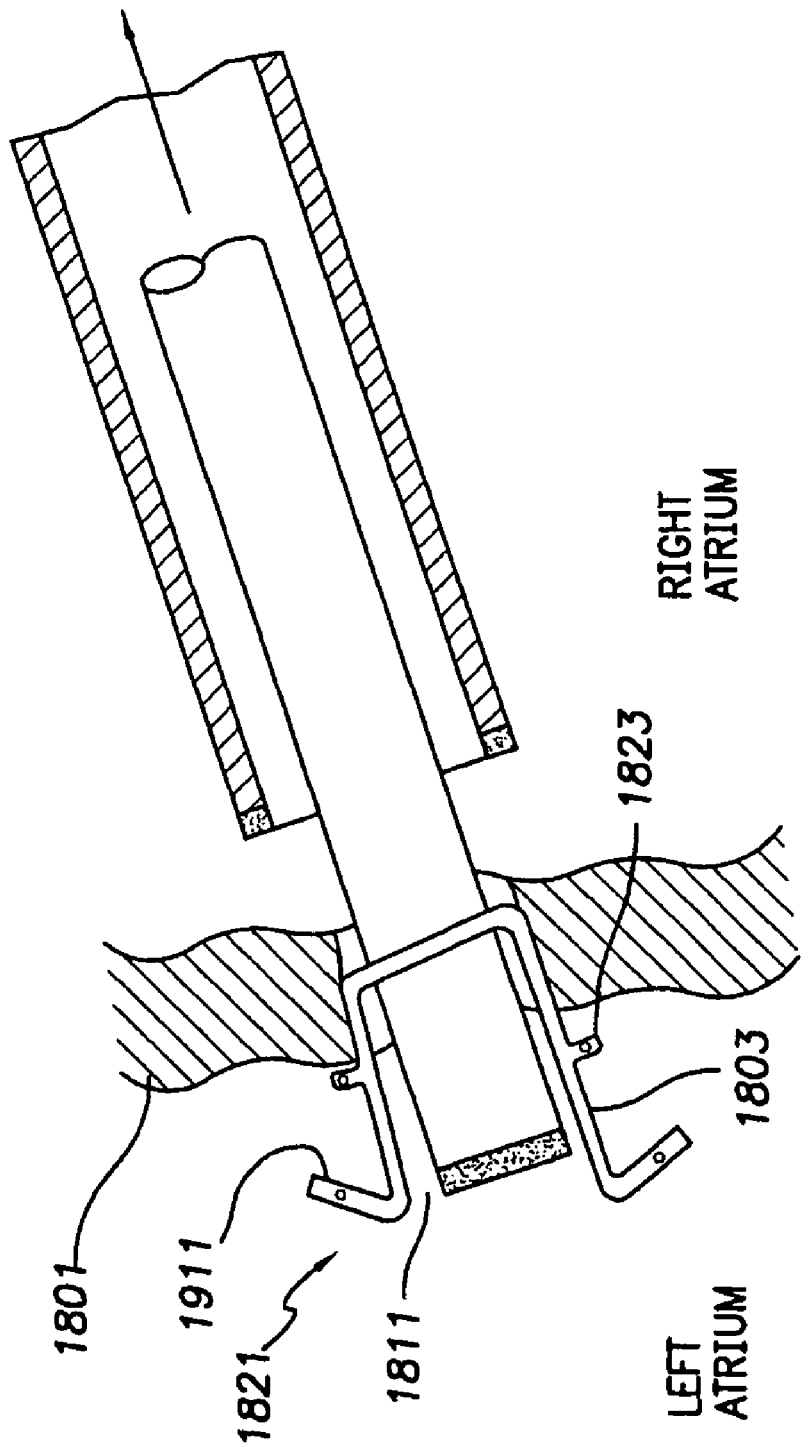
FIG. 20 is an illustration of one embodiment of a head portion of a lead being retracted through a septal wall.
Figure 21:
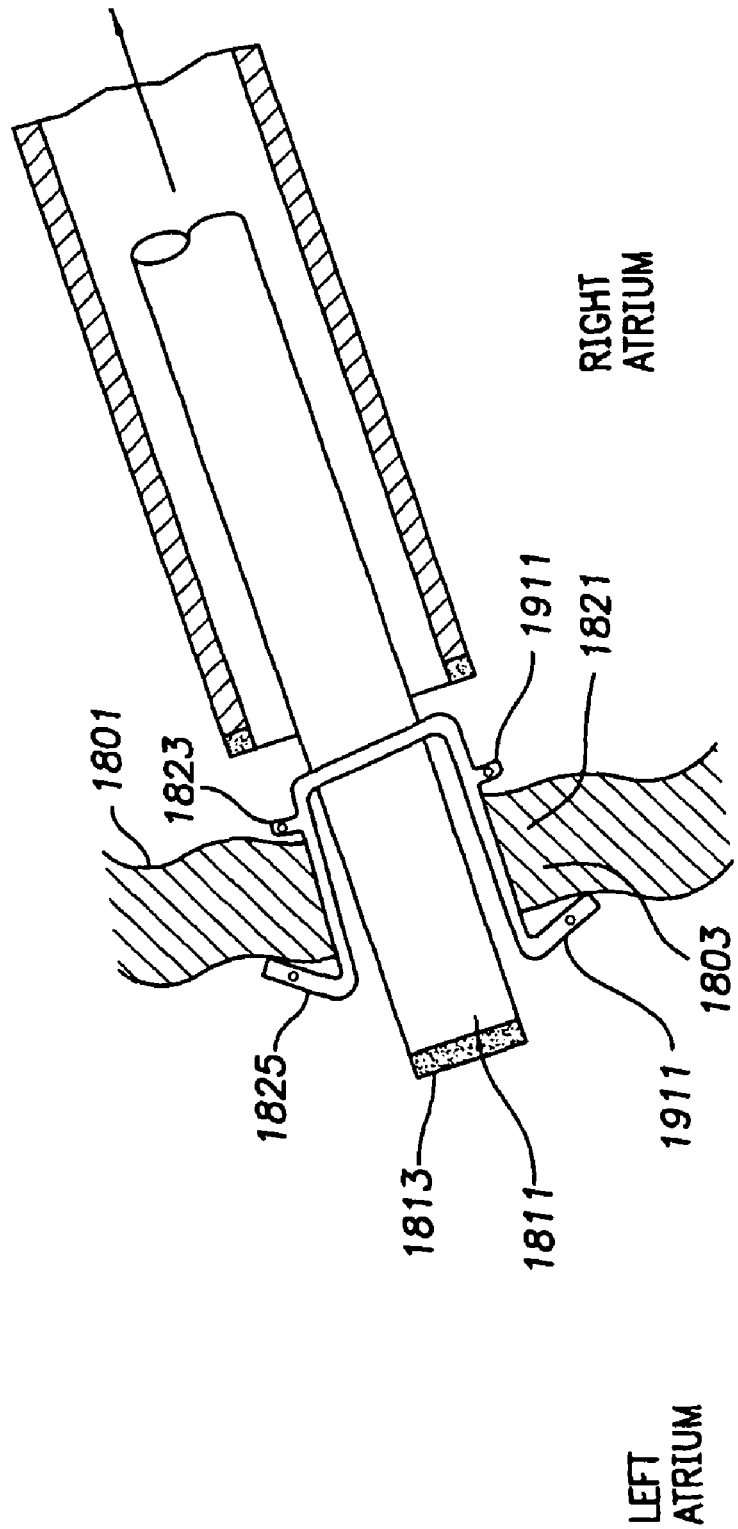
FIG. 21 is an illustration of one embodiment of a head portion of a lead locked into a septal wall.
Figure 24:
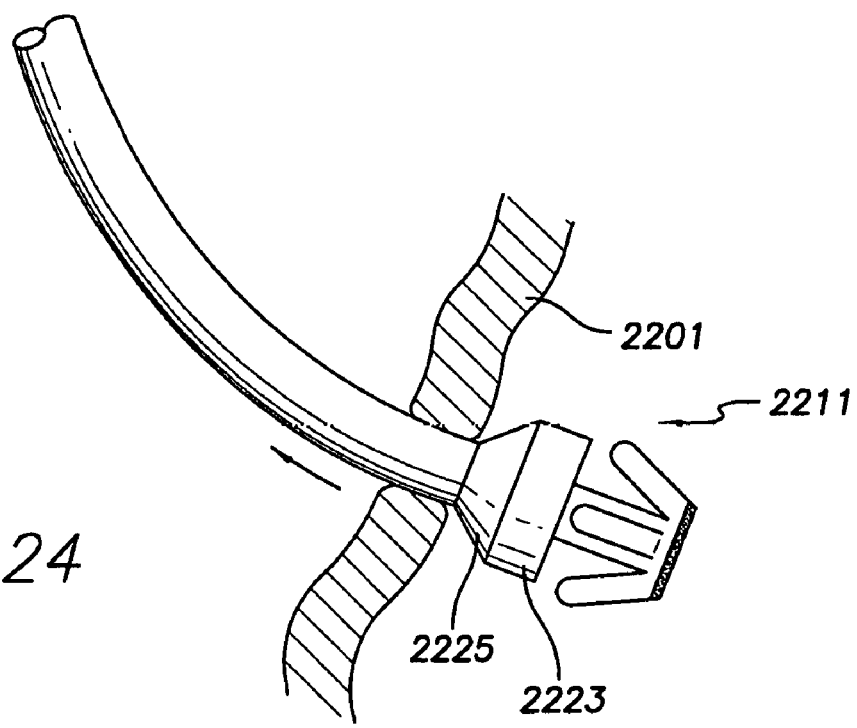
FIG. 24 is an illustration of one embodiment of a head portion of a lead being retracted through a septal wall.

In one embodiment, after the catheter has been retracted, the lead may start to be retracted. The mounting mechanism may start to catch on the septal wall during the retraction. FIGS. 20 and 24 illustrate two embodiments of this phase of the process. Referring to FIG. 20, the arms 1821 of the mounting mechanism 1811 begin to flex toward the tip of the head portion 1811 as the resistance of the septal wall 1801 catches the small protrusions 1823 of the arms 1821. Referring to FIG. 24, as the lead is retracted the proximal anchor 2223 presses against the septal wall 2201. The tapered portion 2225 of the proximal anchor 2223 begins to spread the opening in the septal wall 2201.

In one embodiment, the lead is further retracted to a locked position with respect to the septal wall and the mounting mechanism (block 1521). FIGS. 21 and 25-28 illustrate a set of embodiments in the locked or secured position. In reference to FIG. 21, the mounting mechanism 1803 has locked into place in the septal wall 1801. The small protrusions 1821 on the arms 1821 have slipped through the septal wall 1801. The larger protrusions 1825 abut the septal wall 1801 on one side with the small protrusions 1823 abutting the septal wall 1801 on the other side thereby holding the head portion 1811 in place. The locked position of the mounting mechanism 1803 positions the sensor 1813 in the left atrium with a low profile. The secured position can be confirmed by detecting the location of the arms using the attached or embedded markers 1911 using fluoroscopy. The low profile is achieved due to the position of the larger protrusions 1825. The larger protrusions are roughly in the same plane or lower than that of the surface of the sensor 1813, because the arms 1821 have a length roughly matching the length of the sensor housing 1813 at the tip of the lead and are attached at the base of the sensor 1813.

Figure 25:
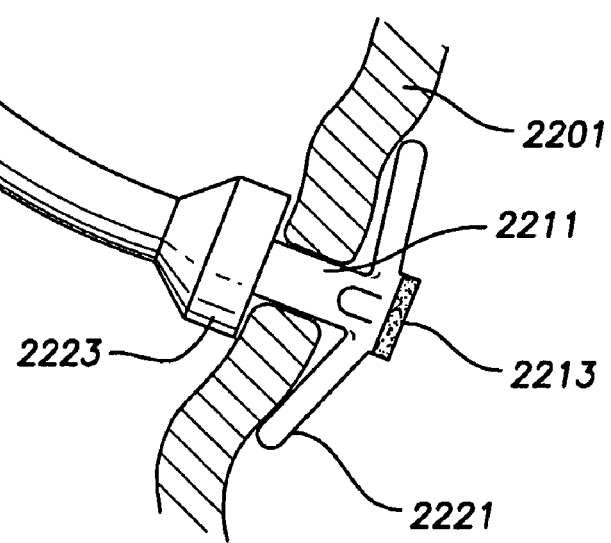
FIG. 25 is an illustration of head portion of a lead locked into a septal wall.

Referring to FIG. 25, the proximal anchor 2223 has slipped through the hole in the septal wall 2201 to place the mounting mechanism in a locked position. The septal wall encircles the gap between the proximal anchor 2225 and the distal anchor 2221. The distal anchor 2221 includes a set of tines spread flat against the septal wall 2201 and presses the septal wall between the distal anchor and the proximal anchor to hold the head portion 2211 in place. The locked position places the sensor 2213 in the left atrium with a low profile.

Figure 26:
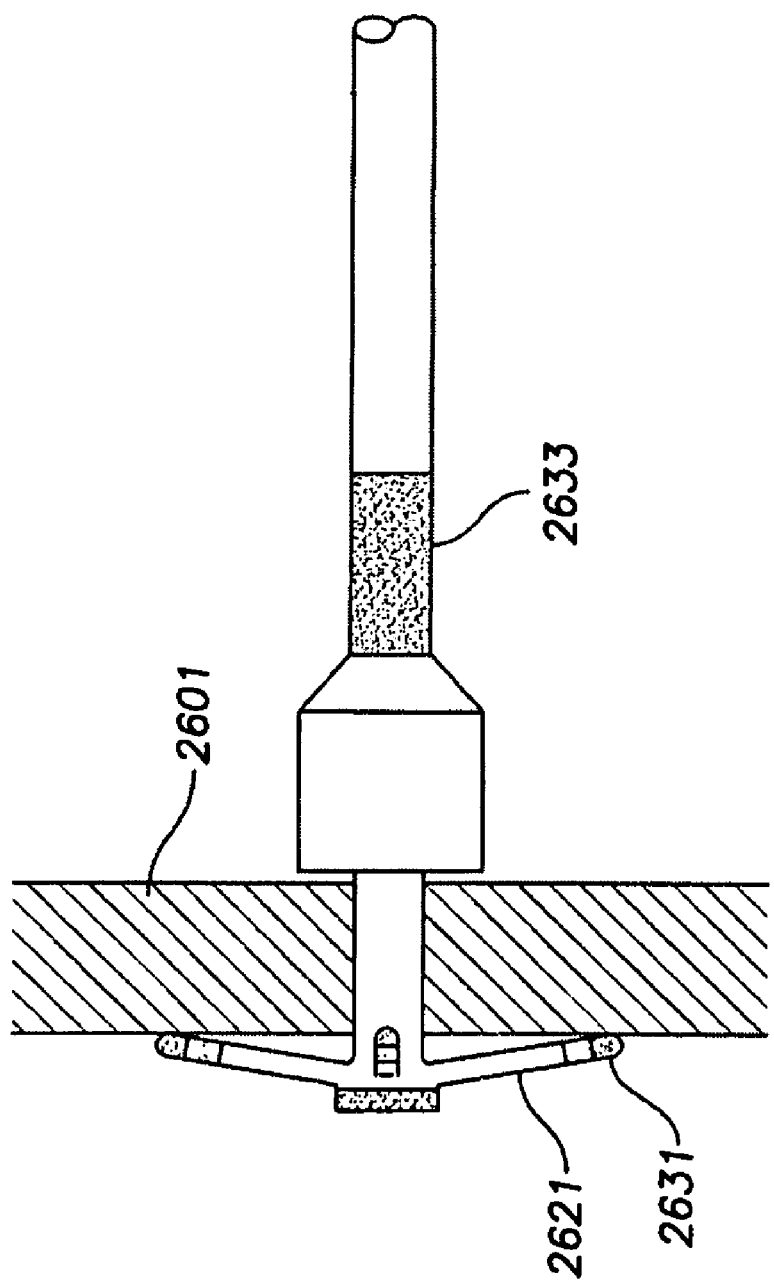
FIG. 26 is an illustration of a lead secured in the septal wall.

FIG. 26 is an illustration of one embodiment of a head portion with a mounting mechanism in a locked position. This embodiment is similar to the embodiment illustrated in FIG. 25. In addition, this embodiment includes a first set of electrodes 2631 on the tips of the tines 2621. In the locked position, the electrodes 2631 in the tines 2621 are pressed against the septal wall in the left atrium. The electrodes 2631 in the tines 2621 may be cathode electrodes. A second electrode 2633 may be positioned in the base portion of the lead. This second electrode 2633 may be an anode electrode. The two sets of electrodes may work independently or together to provide therapeutic electrical signals to the heart for pacing, defibrillation and similar therapeutic actions.

FIG. 27 is an illustration of one embodiment of a head portion with a mounting mechanism in a locked position. This embodiment is similar to the embodiment illustrated in FIG. 25. In addition, this embodiment includes a first electrode 2731 in the head portion between the distal anchor and the proximal anchor. The first electrode 2731 is positioned in the hole in the septal wall 2701. The first electrode 2731 may be a cathode electrode. A second electrode 2733 may be positioned in the base portion of the lead. This second electrode 2733 may be an anode electrode. The two electrodes may work independently or together to provide therapeutic electrical signals to the heart for pacing, defibrillation and similar therapeutic actions.

FIG. 28 is an illustration of one embodiment of a head portion with a mounting mechanism in a locked position. This embodiment is similar to the embodiment illustrated in FIG. 25, except that the proximal anchor is a set of tines 2827. In addition, this embodiment includes a first set of electrodes 2831 in the tips of the proximal tines 2827. The first set of electrodes 2831 is positioned adjacent to the septal wall 2801. The first set of electrodes 2831 may be cathode electrodes. A second electrode 2833 may be positioned in the base portion of the lead. This second electrode 2833 may be an anode electrode. The two sets of electrodes may work independently or together to provide therapeutic electrical signals to the heart for pacing, defibrillation and similar therapeutic actions.

In one embodiment, after the lead has been advanced into place in the septal wall with the sensor in the left atrium, the mounting mechanism maintains the position of the sensor in the left atrium and minimizes the profile of the sensor. The mounting mechanism is positioned in the wall in a manner that may prevent the lead and sensor from moving relative to the wall. In this way, the mounting mechanism serves to effectively hold the lead and sensor in the proper position.

In one embodiment, after the mounting mechanism has been set, the catheter may be removed from the patient leaving the lead in place (block 1523).

In view of the above, it should be understood that a lead may be constructed using various combinations and modifications of the structures and components described herein. For example, the structure and components described in a given drawing may be used in a lead described in another drawing. In addition, lead components such as sensors, electrodes, mounting mechanisms such as tines may be located at various locations on the lead.

In addition, the structures described herein may be implemented in a variety of ways. For example, the leads described herein may be formed by attaching various components together. Also, the combinations of some of the components which are described herein as being "attached," "connected" "including," "affixed," etc., may be implemented as one or more integral components.

It should be appreciated that the applications discussed herein regarding various embodiments may be applicable to other uses and contexts as well. For example, the leads described above may be implanted across any wall including the atrial septum and/or the ventricular septum. Different embodiments of the external monitoring and control systems described above may include a variety of hardware and software processing components. In some embodiments of the invention, hardware components such as controllers, state machines and/or logic are used in a system constructed in accordance with the invention.

In some embodiments, code such as software or firmware executing on one or more processing devices may be used to implement one or more of the described operations. The signals between sensors and external devices may take several forms. For example, in some embodiments a signal may be an electrical signal transmitted over a wire while other signals may consist of wireless signals transmitted through space. In addition, a group of signals may be collectively referred to as a signal herein. The signals discussed above also may take the form of data. For example, in some embodiments an application program of an external device may send a signal to another application program. Such a signal may be stored in a data memory.

The invention described herein may be used as part of an improved cardiac pressure sensing apparatus. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method of measuring pressure comprising:
forming a hole in a septal wall in a heart;
inserting a lead into the hole in the septal wall to place a sensor through the hole in the septal wall and into a chamber of the heart, the lead having a head portion and a body portion, the head portion having a first body;
advancing the head portion of the lead into the chamber to allow expansion of a set of arms, each of the arms having an elongated member extending outwardly from the first body, each of the arms having a first set of protrusions extending outwardly from the elongated member and a second set of protrusions extending outwardly from the elongated member, the first set of protrusions disposed proximal to the second set of protrusions, each of the arms being moveable between a first position adjacent the body portion and a second position with the first set of protrusions adjacent the sensor, the first and second set of protrusions being inwardly arcuate when in the first position to conform with an outer surface of the body portion, the first and second set of protrusions being outwardly arcuate when in the second position, the first set of protrusions adapted to abut a first side of the septal wall when in the second position and the second set of protrusions adapted to abut a second side of the septal wall when in the second position to secure the lead to the septal wall; and
retracting the head portion to catch the first set of protrusions on the septal wall and position the septal wall between the first set of protrusions and a second set of protrusions.

2. The method of claim 1, further comprising:
compressing the set of arms from a natural position to fit the lead into a sheath.

3. The method of claim 2, further comprising:
removing a sheath from a patient.

4. The method of claim 1, further comprising:
spacing the first set of protrusions and the second set of protrusions to correspond to a width of the septal wall.

5. The method of claim 1, further comprising:
forming the lead from one of silicone rubber and polyurethane.

6. The method of claim 1, further comprising:
hingedly attaching a base of each arm in the set of arms to the first body of the head portion.

7. The method of claim 1, further comprising:
disposing the sensor in the head portion.

8. The method of claim 1, further comprising:
defining a lumen in the head and body portion to house a set of wires to electronically connect the sensor to an external device.

9. The method of claim 1, further comprising:
forming the set of arms to have a material memory with a natural position that is 1-2 mm from the body portion at a first end of each arm.

* * * * *